(12) United States Patent
Hahn et al.

(10) Patent No.: US 8,859,232 B2
(45) Date of Patent: Oct. 14, 2014

(54) GENETICALLY ENCODED PHOTOMANIPULATION OF PROTEIN AND PEPTIDE ACTIVITY

(75) Inventors: Klaus Hahn, Chapel Hill, NC (US); Yi Wu, Farmington, CT (US); Brian Kuhlman, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 70 days.

(21) Appl. No.: 13/381,383

(22) PCT Filed: Jul. 1, 2010

(86) PCT No.: PCT/US2010/040747
§ 371 (c)(1),
(2), (4) Date: Mar. 7, 2012

(87) PCT Pub. No.: WO2011/002977
PCT Pub. Date: Jan. 6, 2011

(65) Prior Publication Data
US 2012/0165204 A1 Jun. 28, 2012

Related U.S. Application Data

(60) Provisional application No. 61/222,204, filed on Jul. 1, 2009.

(51) Int. Cl.
| | | |
|---|---|---|
| C12P 21/04 | (2006.01) | |
| C12N 1/20 | (2006.01) | |
| C12N 1/15 | (2006.01) | |
| C12N 15/00 | (2006.01) | |
| C07H 21/04 | (2006.01) | |
| G01N 33/542 | (2006.01) | |
| C12N 9/16 | (2006.01) | |

(52) U.S. Cl.
CPC .......... *G01N 33/542* (2013.01); *C07K 2319/73* (2013.01); *C12N 9/16* (2013.01)
USPC ... 435/69.7; 435/69.1; 435/320.1; 435/252.3; 536/23.2

(58) Field of Classification Search
USPC ......... 435/69.7, 69.1, 320.1, 252.3; 536/23.2; 506/2
See application file for complete search history.

(56) References Cited

U.S. PATENT DOCUMENTS

| | | |
|---|---|---|
| 2004/0038400 A1 | 2/2004 | Froehlich et al. |
| 2005/0074846 A1 | 4/2005 | Gardner et al. |

OTHER PUBLICATIONS

Christie et al., Science vol. 282, 1698-1701 (1998).*
Christie et al., Proc. Natl. Acad. Sci. USA vol. 96, 8779-8783 (1999).*
International Preliminary Report on Patentability for PCT Application No. PCT/US2010/040747, date of mailing Jan. 12, 2012.
Lee et al., "Surface Sites for Engineering Allosteric Control in Proteins," Science 322:438-442 (2008).
Möglich et al., "Design and Signaling Mechanism of Light-Regulated Histidine Kinases," J. Mol. Biol. 385:1433-1444 (2009).
Schmoll et al., "Envoy, a PAS/LOV Domain Protein of *Hypocrea jecorina* (Anamorph *Trichoderma reeseh*, Modulates Cellulase Gene Transcription in Response to Light," Eucaryot. Cell 4:1998-2007 (2005).
Strickland et al., "Light-activated DNA binding in a designed allosteric protein," Proc. Natl. Acad. Sci. U.S.A. 105:10709-10714 2008.
Wu, "Genetically encoded caging—a photoactivatable Rac1," Slide presentation at the 47th Annual American Society for Cell Biology Meeting, Washington DC, Dec. 1-5, 2007.
Wu et al., "Genetically encoded caging—a photoactivatable Rac1," Poster presented at the 48th Annual American Society for Cell Biology Meeting, San Francisco, CA Dec. 13- 17, 2008.

\* cited by examiner

*Primary Examiner* — Chih-Min Kam
(74) *Attorney, Agent, or Firm* — Myers Bigel Sibley & Sajovec, P.A.

(57) ABSTRACT

The present invention relates to fusion proteins comprising protein light switches and methods of photomanipulating the activity of the proteins. The invention further relates to polynucleotides and vectors encoding the fusion proteins, cells comprising the fusion proteins, and methods of using the fusion proteins to study protein function and analyze subcellular activity, as well as diagnostic and therapeutic methods.

19 Claims, 15 Drawing Sheets

FIGS. 2A-2C
a
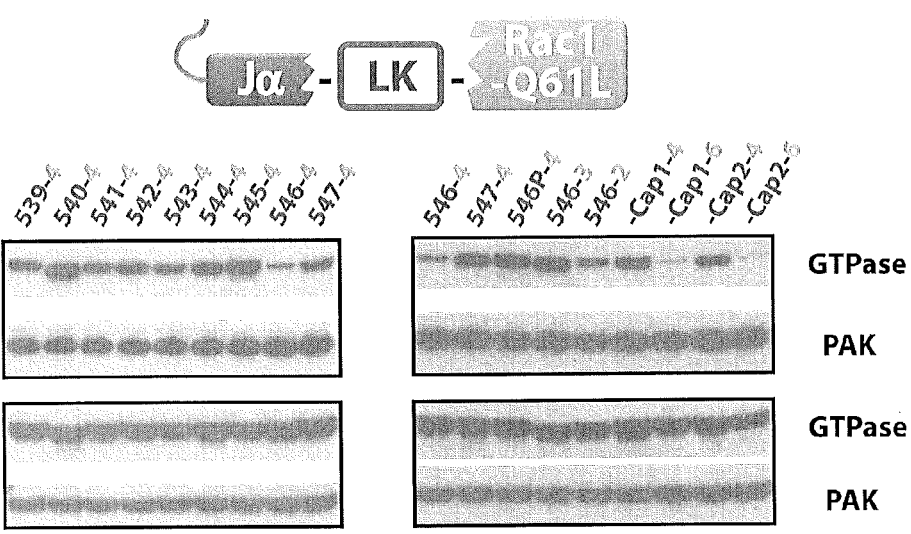
b c
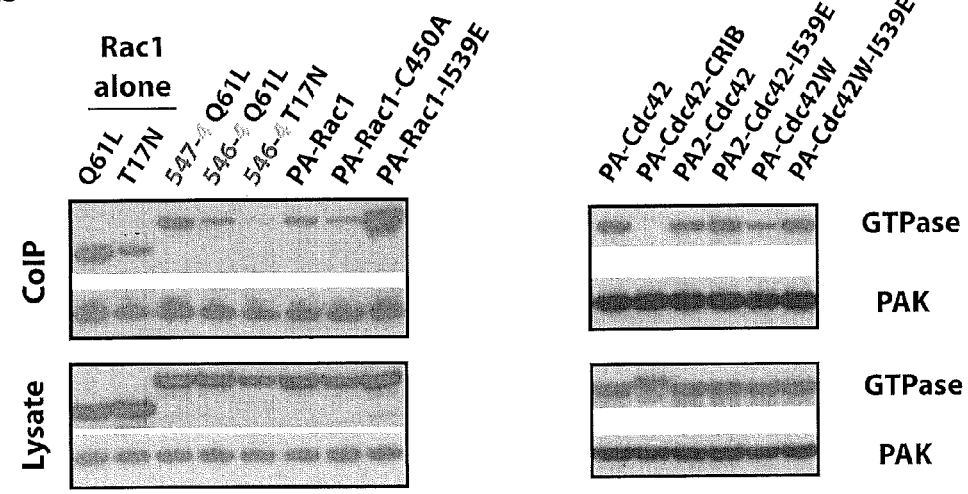

a b c d

FIGS. 9A-9B
A
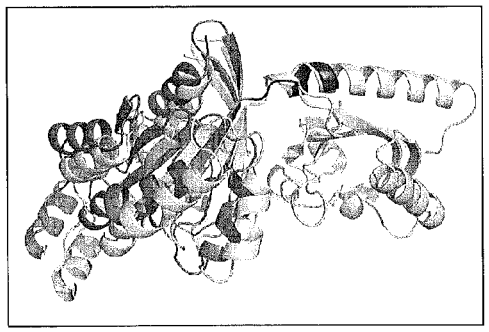
B
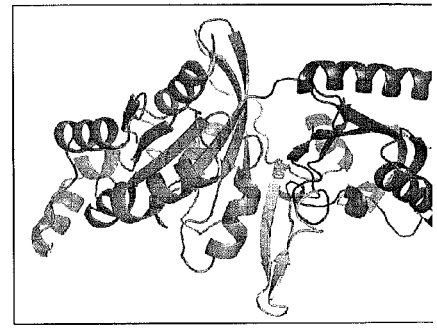
FIG. 10
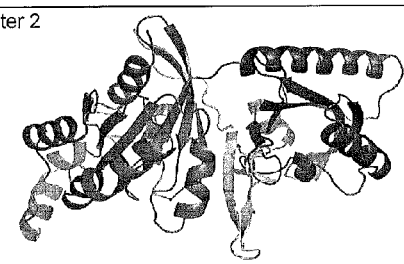
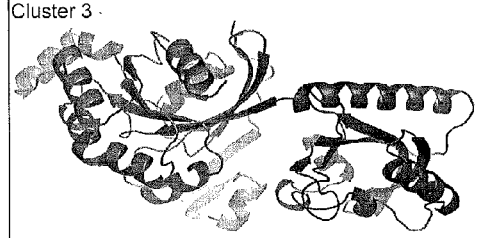
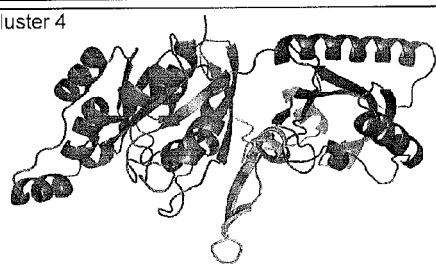
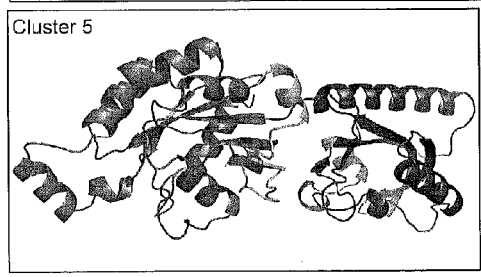

whole cell induction of filopodia local induction of filopodia induction of dorsal filopodia

Sequences of aureochrome used for protein engineering

GENETICALLY ENCODED PHOTOMANIPULATION OF PROTEIN AND PEPTIDE ACTIVITY

RELATED APPLICATIONS

This application is a 35 U.S.C. §371 national phase application of PCT Application PCT/US2010/040747, filed Jul. 1, 2010, which claims the benefit under 35 U.S.C. §119(e) of U.S. Provisional Patent Application Ser. No. 61/222,204, filed Jul. 1, 2009. The entire contents of each of these applications is incorporated herein by reference.

STATEMENT OF FEDERAL SUPPORT

This invention was made with government support under grant numbers GM082288, GM057464, GM064346 and GM073960 awarded by The National Institutes of Health. The government has certain rights in the invention.

FIELD OF THE INVENTION

The present invention relates to fusion proteins comprising protein light switches and methods of photomanipulating the activity of the proteins. The invention further relates to polynucleotides and vectors encoding the fusion proteins, cells comprising the fusion proteins, and methods of using the fusion proteins to study protein function and analyze subcellular activity, as well as diagnostic and therapeutic methods.

BACKGROUND OF THE INVENTION

Protein activity has been photomodulated through a variety of means in living cells, including site-specific derivatization with photocleavable moieties (Goeldner and Givens, *Dynamic Studies in Biology: Phototriggers, Photoswitches and Caged Biomolecules*. (Wiley-VCH, 2005)) or photomodulation of small molecule ligands (Fortin et al., *Nature Methods* 5:331 (2008)). These techniques suffer from some combination of disadvantages preventing widespread application to intracellular proteins—irreversible activation, irradiation with toxic UV light, and/or the need to introduce caged proteins through mechanical disruption of the cell membrane.

Recent NMR studies by Harper et al. revealed the mechanism of a protein light switch in *Avena sativa* (oat) Phototropin1 (Harper et al., *Science* 301:1541 (2003); Yao et al., *Nature Chemical Biology* 4:491 (2008)). The switch consists of a flavin-binding LOV2 (light, oxygen or voltage) domain that interacts with a C-terminal helical extension (Jα) in the dark. Photon absorption results in formation of a covalent bond between Cys450 and the flavin chromophore, causing conformational changes that propagate through the LOV domain, resulting in dissociation and unwinding of the Jα helix.

The present invention addresses previous shortcomings in the art by providing a strategy that enables genetic encoding of the caged protein for ready introduction into cells with reversible activation at less toxic wavelengths.

SUMMARY OF THE INVENTION

The present invention is based, in part, on the identification of methods for regulating the activity of proteins of interest using a protein light switch. Because the regulatable switch is genetically encoded, it provides multiple advantages over prior art caged proteins, including the ability to express the caged protein in a cell instead of having to introduce the protein itself into the cell, the ability to produce large amounts of the caged protein, the ability to have reversible caging, and the ability to activate proteins at less toxic wavelengths. The fusion proteins of the invention permit localized activation of proteins in subcellular locations, providing tremendous opportunities to study protein and cell function as well as maintain tight regulatable control over protein activation for research, diagnostic, and therapeutic purposes.

Accordingly, as one aspect, the invention provides fusion proteins comprising a protein of interest fused to a protein light switch, wherein illumination of the fusion protein activates or inactivates the protein of interest.

In another aspect, the invention relates to polynucleotides and vectors encoding the fusion proteins of the invention.

In a further aspect, the invention relates to host cells comprising the polynucleotides and vectors of the invention and expressing the fusion proteins of the invention.

In another aspect, the invention relates to methods of producing the fusion proteins of the invention, comprising expressing the fusion protein encoded by the polynucleotides and/or vectors of the invention.

In an additional aspect, the invention relates to cells comprising the fusion proteins of the invention.

In a further aspect, the invention relates to methods of producing a protein of interest that is activatable or inactivatable by illumination, comprising fusing the protein of interest to a protein light switch.

In another aspect, the invention relates to methods of activating or inactivating a protein of interest present in the fusion proteins of the invention, comprising illuminating the fusion protein.

In an additional aspect, the invention relates to methods for assessing the function of a protein of interest present in the fusion proteins of the invention, comprising illuminating the protein and assessing one or more activities of the protein of interest.

In a further aspect, the invention relates to fusion proteins comprising a protein of interest, a targeting sequence, and a protein light switch fused together, wherein illumination of the fusion protein exposes or hides the targeting sequence.

In another aspect, the invention relates to methods of targeting a protein of interest to a location in a regulatable manner, comprising illuminating the fusion proteins of the invention to expose the targeting sequence.

In an additional aspect, the invention relates to fusion proteins comprising a target protein binding sequence fused to a protein light switch, wherein illumination of the fusion protein exposes or hides the target protein binding sequence.

In a further aspect, the invention relates to methods of delivering a target protein binding sequence to a protein, comprising illuminating the fusion proteins of the invention to expose the target protein binding sequence, thereby allowing the target protein binding sequence to bind to the target protein.

In another aspect, the invention relates to methods of delivering a target protein binding sequence to a target protein, comprising illuminating the fusion proteins of the invention to expose the target protein binding sequence, thereby allowing the target protein binding sequence to bind to the target protein.

In an additional aspect, the invention relates to methods of manipulating the activity of a target protein, comprising contacting the target protein with the fusion proteins of the invention and illuminating the fusion protein to expose the target protein binding site, wherein the fusion protein binds to the target protein and activates or inactivates the target protein.

In another aspect, the invention relates to methods of regulating the interaction of two proteins of interest, comprising illuminating a pair of fusion proteins comprising a protein of interest fused to a protein light switch comprising a dimerization domain.

In a further aspect, the invention relates to libraries of fusion proteins comprising a library of peptides each fused to a protein light switch.

In another aspect, the invention relates to methods for identifying a fusion protein that can manipulate the activity of a target protein in a regulatable manner, comprising contacting the target protein with a library of fusion proteins of the invention in the absence and presence of illumination, and identifying fusion proteins that exhibit differential binding to the target protein in the absence and presence of illumination.

BRIEF DESCRIPTION OF THE DRAWINGS

FIG. 1A shows a cartoon representation of PA-Rac1 design. Effector binding sites on Rac1 are sterically blocked by the LOV2 domain. Upon irradiation, the Jα helix unwinds, freeing Rac1 activity. When irradiation is stopped, the Jα helix reforms and Rac1 is once again inhibited. FIG. 1B shows pulldown of PA-Rac1 constructs with PAK in the dark. Truncations of LOV and Rac at their linkage point were tested to optimize inhibition of interaction with PAK: 539-547, in red=the terminal amino acid residue of Jα; 2-4, in green=the first residue of Rac1 included in the construct. 546-4 showed the strongest inhibition; PA-Rac1=546-4, Q61L/E91H/N92H (mutations for constitutive activity and to block interactions with regulatory molecules); -C450A, light-insensitive mutant; -I539E, lit state mutant. Loading levels that show pulldown by both constitutively active (Q61L) and dominant negative (T17N) Rac mutants are included for comparison with the extent of activation and inhibition in PA-Rac1. FIG. 1C shows whole cell irradiation of a HeLa cell expressing PA-Rac1. Differential contrast interference (DIC) images at time 0 and closeups at 0, 1, 2, 3 and 4 minutes after irradiation (short axis of box=20 μm). FIG. 1D shows kymograph analyses comparing protrusion of HeLa cells expressing PA-Rac1, its C450A mutant, and the LOV domain alone. Cells were irradiated for 5 minutes at 515 nm (a wavelength not affecting LOV) followed by 5 min at the activating wavelength of 458 nm. The maximum increase in kymograph width over the average width prior to 515 nm irradiation was recorded for >104 kymographs and >10 cells per bar. PA-Rac1 induced protrusions Were more than 4 times as long as those from controls (means+/−95% confidence intervals, short axis of kymograph=20 μm). FIG. 1E shows spatial control of Rac1 activity. A 20-μm circle (dark gray) was irradiated every 60 seconds in MEF cells grown in reduced serum medium. Solid line=cell border at time 0, dotted line=10 minutes after initial light pulse. Little movement of the cell border was detected in these serum-starved cells, except adjacent to the point of irradiation. The kymograph, taken using the white line (20 μm), shows the initial formation of ruffles after each pulse, followed by protrusion (arrowheads=irradiation pulses). FIG. 1F shows diffusion of PA-Rac1 relative to dark inactivation rate. FRAP and the diffusion of PA-Rac1 labeled with PA-GFP were assayed in 10 μm diameter circles (solid lines) and adjacent circles (FIG. 5A) in MEF cells. Dotted lines show the estimated level of activity in the irradiated spot and in an adjacent 10 micron spot, based on the dark recovery rate of LOV.

FIGS. 2A-2C shows screening of PA-Rac1 and PA-Cdc42 in PAK pull-down experiments. FIGS. 2A and 2B show screening of PA-Rac constructs by co-immunoprecipitation with PAK in the dark. 539-547 (red) indicates the terminal amino acid residue of the Jα; 4-2 (green) indicates the starting residue of Rac1; Cap1 and 2 (gray) are inserted Schellman cap linkers; PA-Rac1=546-4 Q61L/E91H/N92H; —C450A=light-insensitive mutant of PA-Rac1; -I539E=lit state mutant of PA-Rac1. FIG. 2C shows engineering of PA-Cdc42. PA-Cdc42=546-4 fusion of LOV and Cdc42; CRIB=control in which the CRIB sequence from PAK was linked to PA-Cdc42; PA2-Cdc42=546-4/E518R/V520F/A524D; PA-Cdc42W=546-4/F56W.

FIG. 3A, lit state mutant (I539E): $K_d=2.2\times10^{-1}\pm1.4\times10^{-2}$ μM, N=0.95±5.7×10$^{-3}$; FIG. 3B, dark state mutant (C450A): $K_d=2.3\pm0.36$ μM, N=1.0±5.1×10$^{-2}$.

FIG. 5A shows the average intensities in the adjacent and irradiated spots, both normalized to the initial intensity of the irradiated spot (means+/−95% confidence intervals). FIG. 5B shows the dark recovery rate of PA-Rac1 at room temperature obtained as previously described (Salomon et al., *Biochemistry* 39:9401 (2000)) ($t_{1/2}$=43 s). This decay rate (which is likely faster at 37° C.) was used to compute the level of active species present in each spot over time (exponential decay of the concentrations indicated in FIG. 5A). The curves show the estimated relative activities in the two adjacent regions, irradiated and nonirradiated.

FIG. 6A shows a protrusion/retraction map after a single pulse of activating illumination (throughout FIG. 6, irradiation=light gray spot, 458 nm, Ø=10 μm). MEFs expressing PA-Rac1 (left) generated protrusions at the site of irradiation (red) and retraction at the opposite side of the cell (blue) (in all 50 cells studied). Irradiation of the dominant negative T17N mutant of PA-Rac1 (right) produced retraction near the point of irradiation, with protrusion in area(s) other than the site of irradiation (in all 25 cells studied). FIG. 6B shows that repeated activation of PA-Rac1 at the cell edge induces directional migration. Irradiation of MEF at 2 minute intervals led to movement in the direction of the light pulse. The cell centroid moved an average of 0.8 microns per pulse (red=protrusion, blue=retraction, green=area overlapping throughout the experiment; n=6). FIG. 6C shows the localized activation of PA-Rac1 in the presence of ML-7 (MLCK inhibitor, 1 µM), Blebbistatin (Myosin II ATPase inhibitor, 1 µM), or Y-27632 (ROCK inhibitor, 10 µM). Cells treated with inhibitor were irradiated and analyzed for protrusion area as in FIG. 6A. Consistent with previous experiments (FIG. 1D), light-induced protrusion was abolished using the photo-inactive C450M mutant, and using the dominant negative T17N mutant of Rac1. Inhibition of myosin had little effect, but ROCK inhibition strongly reduced protrusion. FIG. 6D shows the effect of myosin or ROCK inhibition on the ability of Rac1 to specify the direction of movement. As used previously (Ghosh et al., Science 304:743 (2004)), the cosine of the angle between two lines, that from the irradiation spot to the cell centroid at time 0, and that from the centroid at time 0 to the centroid at the end of the experiment, indicated how much the cell deviates from the direction of movement specified by local irradiation. Using no inhibitors, irradiation of PA-Rac1 produced a cos of nearly 1, indicating that Rac1 controlled the direction of movement. In contrast to effects on protrusion (FIG. 6C), ROCK inhibition had little effect, while inhibition of myosin II caused randomization of movement. Consistent with FIG. 6A, the dominant negative mutant reversed the direction of movement. (panels c and d, n>25).

FIGS. 7A and 7B show PA-Rac1 activation in cells expressing a RhoA biosensor. HeLa cells expressing biosensor and either PA-Rac1 or its C450M photo-inactive mutant were illuminated in a 10-µm circle with a single pulse of 473 nm light. Changes in the FRET efficiency ($E_{corr}$) of the RhoA biosensor, indicative of RhoA activation, are shown in pseudocolored images and as plots of average FRET efficiency within the irradiated circle (blue) and a nearby circle (red). In the PA-Rac1 cells, the irradiated spot showed bleaching of the biosensor followed by a relatively constant level of reduced RhoA activity. In contrast the nearby spot showed no bleaching, but a gradual decrease in RhoA activity reaching the low level achieved in the irradiated spot (n=3 cells). In the control cells (C450M), the biosensor returned to near initial activation readouts after bleaching, and no change was seen in the nearby spot (n=3). FIG. 7C shows RhoA activation in a normal ruffle. As reported previously (Pertz et al., Nature 440: 1069 (2006); Kurokawa et al., Mol. Biol. Cell 16:4294 (2005)), RhoA activation is high in constitutive ruffles at the cell's leading edge. The pseudocolored images show RhoA localization (left, YFP acceptor fluorescence of the biosensor) and RhoA activation (right). The line scan, taken along the white line in the images (red=YFP, blue=Rho activation; line length 78 µm) shows the Rho activation in the ruffle at the cell edge. The asterisk shows the position of the ruffle, and the bold line shows the previously reported inactive RhoA near the nucleus. FIG. 7D shows ruffles generated by PA-Rac1 activation. When ruffles were generated by PA-Rac1 (473 nm irradiation of 20-µm circle shown), their morphology and behavior were different from constitutive ruffles. They translocated much further towards the nucleus, and did not show RhoA activation (line=68 µm, n=6 cells).

FIG. 8A shows the crystal structure of PA-Rac1. Blue=LOV domain, red=Jα helix, and green=Rac1. In the dark state LOV forms an extensive interface with Rac partially blocking the switch region essential for Rac interaction with effectors and upstream regulatory molecules. FIG. 8B shows structural modeling of the effect of LOV2-Rac1 linkers on the Rac1-effector interaction. Models of interaction between the CRIB domain (a Rac effector docking motif, orange) and PA-Rac1 (green, blue and red) showed that shortening or lengthening the LOV2-Rac1 linker by 1 residue opens the binding site to effector interaction (red and green text indicate terminal residue of LOV2 and Rac1 respectively). This is consistent with pulldown results in which only the 546-4 construct (middle panel) was effective at blocking PAK interaction. FIG. 8C shows the interface between LOV2 and Rac1. The crystal structure and modeling revealed hydrophobic interactions and water-mediated hydrogen bonds between Rac1 and the dark state of LOV2, including interactions involving the Rac Trp56 shown. FIG. 8D shows mutation of Cdc42 to increase effectiveness of steric inhibition by LOV. As in FIG. 1B, PAK was used to pulldown LOV2-Cdc42 fusion. Mutating Cdc42 to include the Trp involved in stabilizing the LOV2-Rac1 interaction substantially improved LOV inhibition of Cdc42. Lane 1, PA-Cdc42; linking LOV to Cdc42 using the same truncations that produced good inhibition of PAK binding for Rac does not inhibit Cdc42-PAK binding. Lane 2, PA-Cdc42-CRIB; covalently linking the CRIB domain of PAK to PA-Cdc42 blocks PAK binding. Lane 3, PA-Cdc42-F56W; introduction of the tryptophan substantially improves LOV inhibition of Cdc42 binding to PAK. Lane 4, lit state mutant of PA-Cdc42-F56W, showing that Cdc42 inhibition is sensitive to the lit/dark state of the LOV domain.

FIGS. 9A-9B show models of the PA-Rac1 and LOV2-Rac1 546-4 construct for CRIB binding. FIG. 9A shows superposition of the X-ray structure of PA-Rac1 (gray) and the 546-4 model with the lowest RMSD to the X-ray structure. LOV2 is in blue, and Rac1 in purple. FIG. 9B shows that the model with the lowest RMSD to the PA-Rac1 X-ray structure is unable to bind the CRIB domain (yellow).

FIG. 10 shows modeling of the LOV2-Rac1 546-4 construct for CRIB binding. Models of the five most populated clusters obtained for the 546-4 constructs were analyzed for their abilities to bind the CRIB domain. Of the 1000 models generated during the simulations, 813 were unable to bind CRIB. The model in the centre of each of these clusters was overlaid with CRIB domain. The RMSD of these centre models to the X-ray structure of PA-Rac1 were shown (Table 3). Red, Rac1; blue, LOV2; and yellow, CRIB.

DETAILED DESCRIPTION OF THE INVENTION

Figures 1A, 1B, 1C, 1D, 1E, 1F:
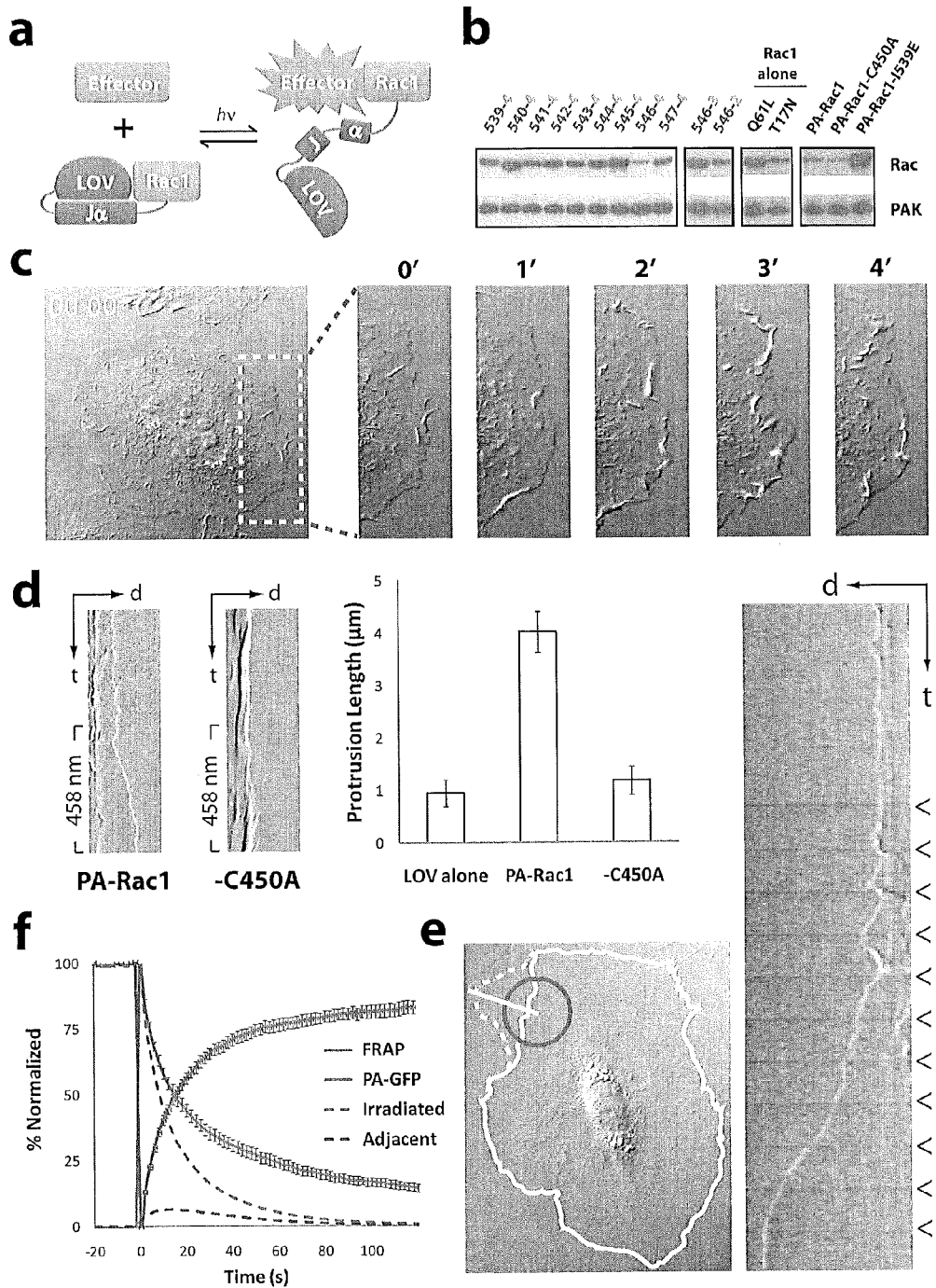
FIGS. 1A-1F show the engineering and in vivo characterization of a photoactivatable Rac1 (PA-Rac1).

The present invention will now be described in more detail with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, patent publications and other references cited herein are incorporated by reference in their entireties for the teachings relevant to the sentence and/or paragraph in which the reference is presented.

Nucleotide sequences are presented herein by single strand only, in the 5' to 3' direction, from left to right, unless specifically indicated otherwise. Nucleotides and amino acids are represented herein in the manner recommended by the IUPAC-IUB Biochemical Nomenclature Commission, or (for amino acids) by either the one-letter code, or the three letter code, both in accordance with 37 C.F.R. §1.822 and established usage.

Except as otherwise indicated, standard methods known to those skilled in the art may be used for cloning genes, amplifying and detecting nucleic acids, and the like. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., New York).

I. DEFINITIONS

As used in the description of the invention and the appended claims, the singular forms "a," "an," and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of polypeptide, dose, time, temperature, enzymatic activity or other biological activity and the like, is meant to encompass variations of ±20%, ±10%, ±5%, ±1%, ±0.5%, or even ±0.1% of the specified amount.

The term "consists essentially of" (and grammatical variants), as applied to a polynucleotide or polypeptide sequence of this invention, means a polynucleotide or polypeptide that consists of both the recited sequence (e.g., SEQ ID NO) and a total of ten or less (e.g., 1, 2, 3, 4, 5, 6, 7, 8, 9, or 10) additional nucleotides or amino acids on the 5' and/or 3' or N-terminal and/or C-terminal ends of the recited sequence such that the function of the polynucleotide or polypeptide is not materially altered. The total of ten or less additional nucleotides or amino acids includes the total number of additional nucleotides or amino acids on both ends added together. The term "materially altered," as applied to polynucleotides of the invention, refers to an increase or decrease in ability to express the encoded polypeptide of at least about 50% or more as compared to the expression level of a polynucleotide consisting of the recited sequence. The term "materially altered," as applied to polypeptides of the invention, refers to an increase or decrease in light-regulatable activity of at least about 50% or more as compared to the activity of a polypeptide consisting of the recited sequence.

The term "activate," as used herein, refers to an increase in at least one biological activity of a protein of interest of the invention, e.g., an increase of at least about 10%, 20%, 30%, 40%, 50%, 60%, 70%, 80%, 90%, 100%, or more.

The term "inactivate," as used herein, refers to a decrease in at least one biological activity of a protein of interest of the invention, e.g., a decrease of at least about 10%, 20%, 30%, 40%, 50%, 60%, 70%, 80%, 90%, 100%, or more.

The term "modulate a protein light switch," as used herein, refers to a physical change in the protein light switch upon illumination that results in a conformational change in the protein light switch.

As used herein, "nucleic acid," "nucleotide sequence," and "polynucleotide" are used interchangeably and encompass both RNA and DNA, including cDNA, genomic DNA, mRNA, synthetic (e.g., chemically synthesized) DNA or RNA and chimeras of RNA and DNA. The term polynucleotide or nucleotide sequence refers to a chain of nucleotides without regard to length of the chain. The nucleic acid can be double-stranded or single-stranded. Where single-stranded, the nucleic acid can be a sense strand or an antisense strand. The nucleic acid can be synthesized using oligonucleotide analogs or derivatives (e.g., inosine or phosphorothioate nucleotides). Such oligonucleotides can be used, for example, to prepare nucleic acids that have altered base-pairing abilities or increased resistance to nucleases. The present invention further provides a nucleic acid that is the complement (which can be either a full complement or a partial complement) of a nucleic acid or nucleotide sequence of this invention.

An "isolated polynucleotide" is a nucleotide sequence (e.g., DNA or RNA) that is not immediately contiguous with nucleotide sequences with which it is immediately contiguous (one on the 5' end and one on the 3' end) in the naturally occurring genome of the organism from which it is derived. Thus, in one embodiment, an isolated polynucleotide includes some or all of the 5' non-coding (e.g., promoter) sequences that are immediately contiguous to a coding sequence. The term therefore includes, for example, a recombinant DNA that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. It also includes a recombinant DNA that is part of a hybrid nucleic acid encoding an additional polypeptide or peptide sequence. An isolated polynucleotide that includes a gene is not a fragment of a chromosome that includes such gene, but rather includes the coding region and regulatory regions associated with the gene, but no additional genes naturally found on the chromosome.

The term "isolated" also can refer to a nucleic acid, nucleotide sequence or polypeptide that is substantially free of cellular material, viral material, and/or culture medium (when produced by recombinant DNA techniques), or chemical precursors or other chemicals (when chemically synthesized). Moreover, an "isolated fragment" is a fragment of a nucleic acid, nucleotide sequence or polypeptide that is not naturally occurring as a fragment and would not be found in the natural state. "Isolated" does not mean that the preparation is technically pure (homogeneous), but it is sufficiently pure to provide the polypeptide or nucleic acid in a form in which it can be used for the intended purpose.

An "isolated" cell refers to a cell that is separated from other components with which it is normally associated in its natural state. For example, an isolated cell can be a cell in culture medium and/or a cell in a pharmaceutically acceptable carrier of this invention. Thus, an isolated cell can be delivered to and/or introduced into a subject. In some embodiments, an isolated cell can be a cell that is removed from a subject and manipulated as described herein ex vivo and then returned to the subject.

The term "fragment," as applied to a nucleic acid, nucleotide sequence, or polynucleotide, will be understood to mean a nucleotide sequence of reduced length relative to a reference nucleic acid or nucleotide sequence and comprising, consisting essentially of, and/or consisting of a nucleotide sequence of contiguous nucleotides identical or almost identical (e.g., 90%, 92%, 95%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of, and/or consist of oligonucleotides having a length of at least about 8, 10, 12, 15, 20, 25, 30, 35, 40, 45, 50, 75, 100, 150, 200, or more consecutive nucleotides of a nucleic acid or nucleotide sequence according to the invention. In other embodiments, such fragments can comprise, consist essentially of, and/or consist of oligonucleotides having a length of less than about 200, 150, 100, 75, 50, 45, 40, 35, 30, 25, 20, 15, 12, 10, 8, or less consecutive nucleotides of a nucleic acid or nucleotide sequence according to the invention.

The term "fragment," as applied to a polypeptide, will be understood to mean an amino acid sequence of reduced length relative to a reference polypeptide or amino acid sequence and comprising, consisting essentially of, and/or consisting of an amino acid sequence of contiguous amino acids identical or almost identical (e.g., 90%, 92%, 95%, 98%, 99% identical) to the reference polypeptide or amino acid sequence. Such a polypeptide fragment according to the invention may be, where appropriate, included in a larger polypeptide of which it is a constituent. In some embodiments, such fragments can comprise, consist essentially of, and/or consist of peptides having a length of at least about 4, 6, 8, 10, 12, 15, 20, 25, 30, 35, 40, 45, 50, 75, 100, 150, 200, or more consecutive amino acids of a polypeptide or amino acid sequence according to the invention. In other embodiments, such fragments can comprise, consist essentially of, and/or consist of peptides having a length of less than about 200, 150, 100, 75, 50, 45, 40, 35, 30, 25, 20, 15, 12, 10, 8, or less consecutive amino acids of a polypeptide or amino acid sequence according to the invention.

A "vector" is any nucleic acid molecule for the cloning of and/or transfer of a nucleic acid into a cell. A vector may be a replicon to which another nucleotide sequence may be attached to allow for replication of the attached nucleotide sequence. A "replicon" can be any genetic element (e.g., plasmid, phage, cosmid, chromosome, viral genome) that functions as an autonomous unit of nucleic acid replication in vivo, i.e., capable of replication under its own control. The term "vector" includes both viral and nonviral (e.g., plasmid) nucleic acid molecules for introducing a nucleic acid into a cell in vitro, ex vivo, and/or in vivo. A large number of vectors known in the art may be used to manipulate nucleic acids, incorporate response elements and promoters into genes, etc. For example, the insertion of the nucleic acid fragments corresponding to response elements and promoters into a suitable vector can be accomplished by ligating the appropriate nucleic acid fragments into a chosen vector that has complementary cohesive termini. Alternatively, the ends of the nucleic acid molecules may be enzymatically modified or any site may be produced by ligating nucleotide sequences (linkers) to the nucleic acid termini. Such vectors may be engineered to contain sequences encoding selectable markers that provide for the selection of cells that contain the vector and/or have incorporated the nucleic acid of the vector into the cellular genome. Such markers allow identification and/or selection of host cells that incorporate and express the proteins encoded by the marker. A "recombinant" vector refers to a viral or non-viral vector that comprises one or more heterologous nucleotide sequences (i.e., transgenes), e.g., two, three, four, five or more heterologous nucleotide sequences.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, adenovirus, geminivirus, and caulimovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, expression control sequences, and/or selectable markers useful in selecting, measuring, and monitoring nucleic acid transfer results (e.g., delivery to specific tissues, duration of expression, etc.).

Vectors may be introduced into the desired cells by methods known in the art, e.g., transfection, electroporation, microinjection, transduction, cell fusion, DEAE dextran, calcium phosphate precipitation, lipofection (lysosome fusion), use of a gene gun, or a nucleic acid vector transporter (see, e.g., Wu et al., *J. Biol. Chem.* 267:963 (1992); Wu et al., *J. Biol. Chem.* 263:14621 (1988); and Hartmut et al., Canadian Patent Application No. 2,012,311, filed Mar. 15, 1990).

In some embodiments, a polynucleotide of this invention can be delivered to a cell in vivo by lipofection. Synthetic cationic lipids designed to limit the difficulties and dangers encountered with liposome-mediated transfection can be used to prepare liposomes for in vivo transfection of a nucleotide sequence of this invention (Feigner et al., *Proc. Natl. Acad. Sci. USA* 84:7413 (1987); Mackey, et al., *Proc. Natl. Acad. Sci. U.S.A.* 85:8027 (1988); and Ulmer et al., *Science*

259:1745 (1993)). The use of cationic lipids may promote encapsulation of negatively charged nucleic acids, and also promote fusion with negatively charged cell membranes (Feigner et al., *Science* 337:387 (1989)). Particularly useful lipid compounds and compositions for transfer of nucleic acids are described in International Patent Publications WO95/18863 and WO96/17823, and in U.S. Pat. No. 5,459, 127. The use of lipofection to introduce exogenous nucleotide sequences into specific organs in vivo has certain practical advantages. Molecular targeting of liposomes to specific cells represents one area of benefit. In representative embodiments, transfection is directed to particular cell types in a tissue with cellular heterogeneity, such as pancreas, liver, kidney, and the brain. Lipids may be chemically coupled to other molecules for the purpose of targeting (Mackey, et al., 1988, supra). Targeted peptides, e.g., hormones or neurotransmitters, and proteins such as antibodies, or non-peptide molecules can be coupled to liposomes chemically.

In various embodiments, other molecules can be used for facilitating delivery of a nucleic acid in vivo, such as a cationic oligopeptide (e.g., WO95/21931), peptides derived from nucleic acid binding proteins (e.g., WO96/25508), and/ or a cationic polymer (e.g., WO95/21931).

It is also possible to introduce a vector in vivo as naked nucleic acid (see U.S. Pat. Nos. 5,693,622, 5,589,466 and 5,580,859). Receptor-mediated nucleic acid delivery approaches can also be used (Curiel et al., *Hum. Gene Ther.* 3:147 (1992); Wu et al., *J. Biol. Chem.* 262:4429 (1987)).

The term "transfection" or "transduction" means the uptake of exogenous or heterologous nucleic acid (RNA and/ or DNA) by a cell. A cell has been "transfected" or "transduced" with an exogenous or heterologous nucleic acid when such nucleic acid has been introduced or delivered inside the cell. A cell has been "transformed" by exogenous or heterologous nucleic acid when the transfected or transduced nucleic acid imparts a phenotypic change in the cell and/or a change in an activity or function of the cell. The transforming nucleic acid can be integrated (covalently linked) into chromosomal DNA making up the genome of the cell or it can be present as a stable plasmid.

As used herein, the terms "protein" and "polypeptide" are used interchangeably and encompass peptides, unless indicated otherwise. In some embodiments, a peptide is a chain of amino acids having a length of about 3 to about 50 residues.

A "fusion protein" is a polypeptide produced when two heterologous nucleotide sequences or fragments thereof coding for two (or more) different polypeptides and/or peptides not found fused together in nature are fused together in the correct translational reading frame. In one embodiment, fusion polypeptides include fusions of a polypeptide of the invention (or a fragment thereof) to a polypeptide that is useful for identifying and/or purifying the fusion protein, e.g., all or a portion of glutathione-S-transferase, maltose-binding protein, or a reporter protein (e.g., Green Fluorescent Protein, β-glucuronidase, β-galactosidase, luciferase, etc.), hemagglutinin, c-myc, FLAG epitope, etc.

As used herein, a "functional" polypeptide or "functional fragment" is one that substantially retains at least one biological activity normally associated with that polypeptide (e.g., light-regulatable activity, protein binding, ligand or receptor binding). In particular embodiments, the "functional" polypeptide or "functional fragment" substantially retains all of the activities possessed by the unmodified peptide. By "substantially retains" biological activity, it is meant that the polypeptide retains at least about 50%, 60%, 75%, 85%, 90%, 95%, 97%, 98%, 99%, or more, of the biological activity of the native polypeptide (and can even have a higher level of activity than the native polypeptide). A "non-functional" polypeptide is one that exhibits little or essentially no detectable biological activity normally associated with the polypeptide (e.g., at most, only an insignificant amount, e.g., less than about 10% or even 5%). Biological activities such as protein binding and light-regulatable activity can be measured using assays that are well known in the art and as described herein.

By the term "express" or "expression" of a polynucleotide coding sequence, it is meant that the sequence is transcribed, and optionally, translated. Typically, according to the present invention, expression of a coding sequence of the invention will result in production of the polypeptide of the invention. The entire expressed polypeptide or fragment can also function in intact cells without purification.

II. FUSION PROTEINS

One aspect of the invention relates to fusion proteins comprising, consisting essentially of, or consisting of a protein of interest fused to a protein light switch, wherein illumination of the fusion protein activates or inactivates the protein of interest. In one embodiment, illumination activates the protein of interest. In another embodiment, illumination inactivates the protein of interest. In one embodiment, the activation or inactivation is reversible, i.e., the activation or inactivation is not permanent. In another embodiment, the activation is dose dependent, with increasing illumination increasing the level of activation or inactivation of the protein of interest. In a further embodiment, the illumination is any wavelength that modulates a protein light switch, e.g., visible light, e.g., in the range of about 450 to about 500 nm. In one embodiment, the wavelength of the illumination is one that is not toxic to living cells. In another embodiment, the illumination comprises more than one wavelength, e.g., a range of wavelengths or multiple specific wavelengths.

The protein light switch of the invention can be any protein or peptide comprising, consisting essentially of, or consisting of an amino acid sequence that is responsive to illumination, e.g., that changes structure in response to illumination. In one embodiment, the protein light switch comprises, consists essentially of, or consists of a LOV (light, oxygen or voltage) domain or a portion thereof that retains substantially all of the responsiveness to illumination. The LOV domain can be any LOV domain known in the art. In one embodiment, the LOV domain is a LOV2 domain. In another embodiment, the protein light switch further comprises a Jα domain. In a further embodiment, the protein light switch comprises, consists essentially of, or consists of a LOV domain and a Jα domain, e.g., a LOV2 domain and a Jα domain. In one embodiment, the protein light switch comprises, consists essentially of, or consists of one or more fragments from a phototropin, e.g., phototropin I, e.g., phototropin I from *Avena sativa* (oat). In another embodiment, the protein light switch comprises, consists essentially of, or consists of the LOV2 domain and/or Jα domain from *A. sativa* phototropin I. The *A. sativa* phototropin I nucleotide and amino acid sequence is known in the art and can be found, e.g., in GenBank at accession number AF033096, herein incorporated by reference in its entirety. In one embodiment, the protein light switch comprises, consists essentially of, or consists of a LOV domain from an aureochrome, e.g., aureochrome from the stramenopile algae *Vaucheria frigida*. In certain embodiments, the protein light switch further comprises the coiled-coil domain from aureochrome, which can function as a dimerization domain to bind other fusion proteins comprising a coiled-coil domain. In other embodiments, the protein light switch comprises, consists essentially of, or consists of one or more fragments from an aureochrome, e.g., amino acids 144-348 of *V. frigida* aureochrome. The *V. frigida* aureochrome nucleotide and amino acid sequence is known in the art and can be found, e.g., in GenBank at accession numbers AB272981 and AB252504, herein incorporated by reference in its entirety.

In one embodiment, the protein light switch comprises the wild-type sequence of the protein in which the switch is found in nature. In another embodiment, the protein light switch comprises an amino acid sequence that is modified from the wild-type sequence, e.g., to be responsive to a different wavelength than the wild-type sequence or to bind a different or modified cofactor, e.g., flavin. The amino acids involved in forming the flavin binding pocket of the LOV2 domain have been identified and include, without limitation, V416, T418, N425, N449, C450, R451, L453, Q454, V463, I466, R467, I470, L480, N482, N492, F494, L496, F509, I510, G511, and Q513. One or more of these amino acids can be modified to redesign the flavin binding pocket to accept flavins that absorb light at alternative wavelengths.

In certain embodiments, the LOV-Jα domain can be modified to improve its ability to inhibit the activity of the protein of interest in the dark state. In one embodiment, the amino acid sequence of the LOV-Jα domain is modified to increase the binding between the globular domain and the helix in the dark state. For example the addition of salt-bridge forming mutations (such as L514K and/or L531E) strengthens the binding between the helix and the globular domain and limits "leakiness" in the dark state.

In one embodiment, the fusion protein comprises one or more linkers between different domains of the fusion protein, e.g., between the protein of interest and the protein light switch and/or between the domains of the protein light switch, e.g., between the LOV2 domain and the Jα domain. The linker can be an amino acid sequence of a length suitable to provide sufficient flexibility between the domains of the fusion protein to allow illumination-dependent activation or inactivation of the protein of interest. For example, the linker can comprise, consist essentially of or consist of a peptide of about 3 to about 20 amino acids or more, e.g., about 3, 4, 5, 6, 7, 8, 9, 10, 11, 12, 13, 14, 15, 16, 17, 18, 19, or 20 or more amino acids.

In one embodiment of the fusion proteins of the invention, the protein of interest and the protein light switch each comprise an amino acid sequence that promotes binding of the protein of interest to the protein light switch. Increased binding affinity between the protein of interest and the protein light switch in the inactive (e.g., dark) state enhances the inactivation of the protein of interest and decreases or prevents "leaky" activity. The amino acid sequences that promote binding may be sequences that are present in the wild-type sequence of each domain. In other embodiments, the amino acid sequence of the protein of interest and/or the protein light switch is modified to comprise the amino acid sequence that promotes binding. Amino acid sequences that bind to each other are well known in the art and can be readily incorporated into the fusion proteins. In one embodiment, the surface of the protein light switch can be mutated to form favorable contacts with the protein of interest. In another embodiment, the protein light switch sequence can be extended with residues that have an affinity for the protein of interest, e.g., at the terminus that is not linked to the protein of interest. For example, if the protein of interest is a GTPase, the sequence extension can comprise a known GTPase binding site (e.g., the amino acid sequence EISAP (SEQ ID NO:1) and the entire extension can be the amino acid sequence EISAPSNGTGRGG (SEQ ID NO:2) or EISAPSQGDGG (SEQ ID NO:14). In one embodiment, the extension sequence can be attached to, e.g., the N-terminus of the LOV domain.

The protein of interest in the fusion proteins of the invention can be any known protein of interest. The term "protein of interest" encompasses full length proteins, modified proteins, fragments of proteins, and functional domains of proteins. In one embodiment, the protein of interest is a mammalian protein, e.g., a human protein. In one embodiment, the protein of interest or a functional fragment thereof is selected from a family of proteins, e.g., GTPases (such as Rac1 and Cdc42), guanine nucleotide exchange factors, kinases, transcription factors, integrins, cytoskeletal proteins (e.g., actin and microtubule proteins), and cytoskeleton-associated proteins that are critical in regulation of dynamics (e.g., components of Arp2/3 complex, fascin, cofilin, Ena/VASP and other capping proteins). In another embodiment, the protein of interest or a functional fragment thereof is a functional domain selected from translocation signals (such as nuclear localization signals, nuclear export signals, and organelle targeting domains), binding domains, the catalytic domain of proteinases, kinases, and other enzymes, the ATP binding pocket of kinases and other enzymes, the regulatory domain of kinases and other enzymes (e.g., the RI or RII domain of protein kinase A), the regulatory light chain and/or the ATPase domains of myosin motor proteins, the regulatory light chain and/or the ATPase domains of microtubule-driven motor proteins, the regulatory and/or catalytic domains of kinases, and SH domains. In another embodiment, the protein of interest is a peptide that inhibits the activity of a target protein (e.g., an inhibitor of protein kinase A, protein kinase C, vinculin, etc.). In a further embodiment, the protein of interest is a first member of a protein binding pair.

In representative embodiments, the protein light switch can be fused to either the N terminus or C terminus of the protein of interest or within the protein of interest (e.g., between two domains), as long as the protein light switch is capable of modulating the activity of the protein of interest in an illumination-dependent manner. The distance between the protein of interest and the protein light switch can be adjusted to maximize the ability of the protein light switch to modulate the activity of the protein of interest. For example, a linker can be inserted between the two domains or some of the terminal amino acids of the protein of interest and/or protein light switch can be deleted, e.g., 1, 2, 3, 4, 5, 6, 7, 8, 9, 10 or more amino acids from one or both domains. Additionally, the amino acid sequence of the protein of interest and/or protein light switch can be modified to increase the ability of the protein light switch to modulate the activity of the protein of interest. For example, 1, 2, 3, 4, 5, or more amino acids of the protein of interest and/or protein light switch can be substituted, deleted or added either at the terminus or internally to maximize illumination-dependent regulation.

In another aspect, the protein of interest can be fused within the protein light switch, e.g., within the Jα domain. In one embodiment, the protein of interest can be a peptide (e.g., an activator, inhibitor, localization signal, and/or dimerization motif) that does not disrupt the Jα helix and is inaccessible in either the dark state or the light state and becomes available in the other state. In another aspect, the protein light switch can be fused within the protein of interest. In one embodiment, the portion of phototropin that mediates light-dependent regulation is inserted within the activation loop of a kinase.

Fusion proteins of the invention can be modified for use in cells in vitro, ex vivo, or in vivo by the addition, e.g., at the amino- and/or carboxyl-terminal ends, of a blocking agent to facilitate survival of the relevant polypeptide in the cell or in vivo. This can be useful in those situations in which the protein termini tend to be degraded by proteases prior to cellular uptake. Such blocking agents can include, without limitation, additional related or unrelated peptide sequences that can be attached to the amino and/or carboxyl terminal residues of the protein to be administered. This can be done either chemically during the synthesis of the fusion protein or by recombinant DNA technology by methods familiar to artisans of average skill. Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the fusion proteins can be covalently or noncovalently coupled to pharmaceutically acceptable "carrier" proteins or other molecules (e.g., PEG) prior to administration.

III. POLYNUCLEOTIDE, VECTORS, AND CELLS

One aspect of the invention relates to polynucleotides encoding the fusion proteins of the invention. In one embodiment, the polynucleotide comprises, consists essentially of, or consists of a nucleotide sequence that encodes the fusion proteins of the invention. Polynucleotides of this invention include RNA, DNA (including cDNAs) and chimeras thereof. The polynucleotides can further comprise modified nucleotides or nucleotide analogs. It will be appreciated by those skilled in the art that there can be variability in the polynucleotides that encode the fusion proteins of the present invention due to the degeneracy of the genetic code. The degeneracy of the genetic code, which allows different nucleic acid sequences to code for the same polypeptide, is well known in the literature.

The isolated polynucleotides encoding the fusion proteins of the invention will typically be associated with appropriate expression control sequences, e.g., promoters, enhancers, transcription/translation control signals and polyadenylation signals.

A variety of promoter/enhancer elements can be used depending on the level and tissue-specific expression desired. The promoter can be constitutive or inducible, depending on the pattern of expression desired. The promoter can be native or foreign and can be a natural or a synthetic sequence. By foreign, it is intended that the transcriptional initiation region is not found in the wild-type host into which the transcriptional initiation region is introduced. The promoter is chosen so that it will function in the target cell(s) of interest.

To illustrate, the polynucleotide encoding the fusion protein can be operatively associated with a cytomegalovirus (CMV) major immediate-early promoter, an albumin promoter, an Elongation Factor 1-α (EF1-α) promoter, a PγK promoter, a MFG promoter, or a Rous sarcoma virus promoter.

Inducible promoter/enhancer elements include hormone-inducible and metal-inducible elements, and other promoters regulated by exogenously supplied compounds, including without limitation, the zinc-inducible metallothionein (MT) promoter; the dexamethasone (Dex)-inducible mouse mammary tumor virus (MMTV) promoter; the T7 polymerase promoter system (see WO 98/1'0088); the ecdysone insect promoter (No et al., *Proc. Natl. Acad. Sci. USA* 93:3346 (1996)); the tetracycline-repressible system (Gossen et al., *Proc. Natl. Acad. Sci. USA* 89:5547 (1992)); the tetracycline-inducible system (Gossen et al., *Science* 268:1766 (1995); see also Harvey et al., *Curr. Opin. Chem. Biol.* 2:512 (1998)); the RU486-inducible system (Wang et al., *Nat. Biotech.* 15:239 (1997); Wang et al., *Gene Ther.*, 4:432 (1997)); and the rapamycin-inducible system (Magari et al., *J. Clin. Invest.* 100: 2865 (1997)).

Moreover, specific initiation signals are generally required for efficient translation of inserted protein coding sequences. These translational control sequences, which can include the ATG initiation codon and adjacent sequences, can be of a variety of origins, both natural and synthetic.

The present invention further provides cells comprising the polynucleotides and fusion proteins of the invention. The cell may be a cultured cell or a cell ex vivo or in vivo, e.g., for use in therapeutic methods, diagnostic methods, screening methods, methods for studying the biological action of proteins of interest, methods of producing fusion proteins, or methods of maintaining or amplifying the polynucleotides of the invention, etc. The cell can be e.g., a bacterial, fungal (e.g., yeast), plant, insect, avian, mammalian, or human cell.

The polynucleotide can be incorporated into an expression vector. Expression vectors compatible with various host cells are well known in the art and contain suitable elements for transcription and translation of nucleic acids. Typically, an expression vector contains an "expression cassette," which includes, in the 5' to 3' direction, a promoter, a coding sequence encoding a fusion protein operatively associated with the promoter, and, optionally, a termination sequence including a stop signal for RNA polymerase and a polyadenylation signal for polyadenylase.

Non-limiting examples of promoters of this invention include CYC1, HIS3, GAL1, GAL4, GAL10, ADH1, PGK, PHO5, GAPDH, ADC1, TRP1, URA3, LEU2, ENO, TPI, and alkaline phosphatase promoters (useful for expression in *Saccharomyces*); AOX1 promoter (useful for expression in *Pichia*); β-lactamase, lac, ara, tet, trp, $IP_L$, $IP_R$, T7, tac, and trc promoters (useful for expression in *Escherichia coli*); light regulated-, seed specific-, pollen specific-, ovary specific-, pathogenesis or disease related-promoters, cauliflower mosaic virus 35S, CMV 35S minimal, cassaya vein mosaic virus (CsVMV), chlorophyll a/b binding protein, ribulose 1,5-bisphosphate carboxylase, shoot-specific promoters, root specific promoters, chitinase, stress inducible promoters, rice tungro bacilliform virus, plant super-promoter, potato leucine aminopeptidase, nitrate reductase, mannopine synthase, nopaline synthase, ubiquitin, zein protein, and anthocyanin promoters (useful for expression in plant cells).

Further examples of animal and mammalian promoters known in the art include, but are not limited to, the SV40 early (SV40e) promoter region, the promoter contained in the 3' long terminal repeat (LTR) of Rous sarcoma virus (RSV), the promoters of the E1A or major late promoter (MLP) genes of adenoviruses (Ad), the cytomegalovirus (CMV) early promoter, the herpes simplex virus (HSV) thymidine kinase (TK) promoter, baculovirus IE1 promoter, elongation factor 1 alpha (EF1) promoter, phosphoglycerate kinase (PGK) promoter, ubiquitin (Ubc) promoter, an albumin promoter, the regulatory sequences of the mouse metallothionein-L promoter and transcriptional control regions, the ubiquitous promoters (HPRT, vimentin, α-actin, tubulin and the like), the promoters of the intermediate filaments (desmin, neurofilaments, keratin, GFAP, and the like), the promoters of therapeutic genes (of the MDR, CFTR or factor VIII type, and the like), pathogenesis and/or disease-related promoters, and promoters that exhibit tissue specificity, such as the elastase I gene control region, which is active in pancreatic acinar cells; the insulin gene control region active in pancreatic beta cells, the immunoglobulin gene control region active in lymphoid cells, the mouse mammary tumor virus control region active in testicular, breast, lymphoid and mast cells; the albumin gene promoter, the Apo AI and Apo AII control regions active in liver, the alpha-fetoprotein gene control region active in liver, the alpha 1-antitrypsin gene control region active in the liver, the beta-globin gene control region active in myeloid cells, the myelin basic protein gene control region active in oligodendrocyte cells in the brain, the myosin light chain-2 gene control region active in skeletal muscle, and the gonadotropic releasing hormone gene control region active in the hypothalamus, the pyruvate kinase promoter, the villin promoter, the promoter of the fatty acid binding intestinal protein, the promoter of smooth muscle cell α-actin, and the like. In addition, any of these expression sequences of this invention can be modified by addition of enhancer and/or regulatory sequences and the like.

Enhancers that may be used in embodiments of the invention include but are not limited to: an SV40 enhancer, a cytomegalovirus (CMV) enhancer, an elongation factor I (EF1) enhancer, yeast enhancers, viral gene enhancers, and the like.

Termination control regions, i.e., terminator or polyadenylation sequences, may be derived from various genes native to the preferred hosts. In some embodiments of the invention, the termination control region may comprise or be derived from a synthetic sequence, a synthetic polyadenylation signal, an SV40 late polyadenylation signal, an SV40 polyadenylation signal, a bovine growth hormone (BGH) polyadenylation signal, viral terminator sequences, or the like.

Expression vectors can be designed for expression of polypeptides in host cells, e.g., prokaryotic or eukaryotic cells. For example, polypeptides can be expressed in bacterial cells such as *E. coli*, insect cells (e.g., the baculovirus expression system), yeast cells, plant cells or mammalian cells. Some suitable host cells are discussed further in Goeddel, *Gene Expression Technology*: Methods in Enzymology 185, Academic Press, San Diego, Calif. (1990). Examples of bacterial vectors include pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, and pRIT5 (Pharmacia). Examples of vectors for expression in the yeast *S. cerevisiae* include pYepSec1 (Baldari et al., *EMBO J.* 6:229 (1987)), pMFa (Kurjan and Herskowitz, *Cell* 30:933 (1982)), pJRY88 (Schultz et al., *Gene* 54:113 (1987)), and pYES2 (Invitrogen Corporation, San Diego, Calif.). Baculovirus vectors available for expression of nucleic acids to produce proteins in cultured insect cells (e.g., Sf 9 cells) include the pAc series (Smith et al., *Mol. Cell. Biol.* 3:2156 (1983)) and the pVL series (Lucklow and Summers Virology 170:31 (1989)).

Examples of mammalian expression vectors include pWL-NEO, pSV2CAT, pOG44, pXT1, pSG (Stratagene) pSVK3, PBPV, pMSG, PSVL (Pharmacia), pCDM8 (Seed, *Nature* 329:840 (1987)) and pMT2PC (Kaufman et al., *EMBO J.* 6:187 (1987)). When used in mammalian cells, the expression vector's control functions are often provided by viral regulatory elements. For example, commonly used promoters are derived from polyoma, adenovirus 2, cytomegalovirus and Simian Virus 40.

Viral vectors have been used in a wide variety of gene delivery applications in cells, as well as living animal subjects. Viral vectors that can be used include, but are not limited to, retrovirus, lentivirus, adeno-associated virus, poxvirus, alphavirus, baculovirus, vaccinia virus, herpes virus, Epstein-Barr virus, adenovirus, geminivirus, and caulimovirus vectors. Non-viral vectors include plasmids, liposomes, electrically charged lipids (cytofectins), nucleic acid-protein complexes, and biopolymers. In addition to a nucleic acid of interest, a vector may also comprise one or more regulatory regions, and/or selectable markers useful in selecting, measuring, and monitoring nucleic acid transfer results (delivery to specific tissues, duration of expression, etc.).

In addition to the regulatory control sequences discussed above, the recombinant expression vector can contain additional nucleotide sequences. For example, the recombinant expression vector can encode a selectable marker gene to identify host cells that have incorporated the vector.

Vector DNA can be introduced into prokaryotic or eukaryotic cells via conventional transformation or transfection techniques, including, without limitation, calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al., Molecular Cloning: A Laboratory Manual 2nd Ed. (Cold Spring Harbor, N.Y., 1989), and other laboratory manuals.

If stable integration is desired, often only a small fraction of cells (in particular, mammalian cells) integrate the foreign DNA into their genome. In order to identify and select integrants, a nucleic acid that encodes a selectable marker (e.g., resistance to antibiotics) can be introduced into the host cells along with the nucleic acid of interest. Preferred selectable markers include those that confer resistance to drugs, such as G418, hygromycin and methotrexate. Nucleic acids encoding a selectable marker can be introduced into a host cell on the same vector as that comprising the nucleic acid of interest or can be introduced on a separate vector. Cells stably transfected with the introduced nucleic acid can be identified by drug selection (e.g., cells that have incorporated the selectable marker gene will survive, while the other cells die).

The polynucleotide can also be introduced into a plant, plant cell or protoplast and, optionally, the isolated nucleic acid encoding the polypeptide is integrated into the nuclear or plastidic genome. Plant transformation is known in the art. See, in general, *Meth. Enzymol. Vol.* 153 ("Recombinant DNA Part D") 1987, Wu and Grossman Eds., Academic Press and European Patent Application EP 693554.

According to certain embodiments, the polynucleotides or vectors can be targeted to specific cells or tissues in vivo. Targeting delivery vehicles, including liposomes and viral vector systems are known in the art. For example, a liposome can be directed to a particular target cell or tissue by using a targeting agent, such as an antibody, soluble receptor or ligand, incorporated with the liposome, to target a particular cell or tissue to which the targeting molecule can bind. Targeting liposomes are described, for example, in Ho et al., *Biochemistry* 25:5500 (1986); Ho et al., *J. Biol. Chem.* 262:13979 (1987); Ho et al., *J. Biol. Chem.* 262:13973 (1987); and U.S. Pat. No. 4,957,735 to Huang et al., each of which is incorporated herein by reference in its entirety. Enveloped viral vectors can be modified to deliver a nucleic acid molecule to a target cell by modifying or substituting an envelope protein such that the virus infects a specific cell type. In adenoviral vectors, the gene encoding the attachment fibers can be modified to encode a protein domain that binds to a cell-specific receptor. Herpesvirus vectors naturally target the cells of the central and peripheral nervous system. Alternatively, the route of administration can be used to target a specific cell or tissue. For example, intracoronary administration of an adenoviral vector has been shown to be effective for the delivery of a gene to cardiac myocytes (Maurice et al., *J. Clin. Invest.* 104:21 (1999)). Intravenous delivery of cholesterol-containing cationic liposomes has been shown to preferentially target pulmonary tissues (Liu et al., *Nature Biotechnol.* 15:167 (1997)), and effectively mediate transfer and expression of genes in vivo. Other examples of successful targeted in vivo delivery of nucleic acid molecules are known in the art. Finally, a recombinant nucleic acid molecule can be selectively (i.e., preferentially, substantially exclusively) expressed in a target cell by selecting a transcription control sequence, and preferably, a promoter, which is selectively induced in the target cell and remains substantially inactive in non-target cells.

In one aspect, the invention relates to methods of producing the fusion proteins of the invention, comprising expressing the fusion protein encoded by the polynucleotides and/or vectors described above. In one embodiment, the fusion proteins can be expressed in vitro, e.g., by in vitro transcription and/or translation. In another embodiment, the fusion protein can be expressed in a cell, e.g., an isolated cell, such as a cell line or a primary cell. In a different embodiment, the cell can be present in an animal or plant, e.g., for in vivo production of the fusion protein or for therapeutic or diagnostic purposes.

In one aspect, the invention relates to methods for producing a protein of interest that is activatable or inactivatable by illumination, comprising fusing the protein of interest to a protein light switch. In one embodiment, the fusion protein is produced recombinantly by preparing a polynucleotide encoding the fusion protein. Coding sequences for the fusion proteins of the invention can be prepared using techniques well known in the art, including cutting and splicing polynucleotides encoding domains of the fusion protein or chemically synthesizing all or part of the coding sequence. In another embodiment, the fusion protein can be prepared at the protein level, e.g., by linking peptides or chemically synthesizing all or part of the amino acid sequence.

IV. METHODS

One aspect of the invention relates to methods of activating or inactivating a protein of interest present in a fusion protein of the invention, comprising illuminating the fusion protein, thereby activating or inactivating the protein of interest. The fusion protein is illuminated at an appropriate wavelength or wavelength range and for a sufficient period of time to activate or inactivate the protein of interest. The fusion protein can be repeatedly activated or inactivated by supplying and removing illumination. The level of activation or inactivation can be regulated by controlling the level of illumination. Illumination can be provided by any means known in the art, e.g., by using a broad spectrum white light or a light providing a narrower wavelength range, such as a blue light (e.g., blue AlGaInP LEDs).

In one embodiment, the fusion protein is illuminated in vitro. In another embodiment, the fusion protein is illuminated in a cell, e.g., an isolated cell or a cell in an animal. In one embodiment, the entire cell is illuminated such that most or all of the fusion protein present in the cell is activated or inactivated. In other embodiments, one or more portions of a cell are illuminated such that the fusion protein is activated or inactivated in only a portion of the cell.

In one embodiment, two or more different fusion proteins are illuminated. In another embodiment, different fusion proteins respond to a different wavelength so that the fusion proteins can be individually activated or inactivated.

Another aspect of the invention relates to methods for assessing the function of a protein of interest present in the fusion protein of the invention, comprising illuminating the protein and assessing one or more activities of the protein of interest. Any activity of the protein of interest can be assessed. Examples of measurable activities include, without limitation, protein binding, nucleic acid binding, signaling, translocation, and/or enzymatic activity.

In one embodiment the protein of interest in the fusion proteins of the present invention is a first member of a protein or peptide binding pair. In this embodiment, the protein light switch blocks the binding site on the first member and prevents binding of the first member to the second member of the binding pair. When the first and second binding members create a functional protein when bound together (e.g., the DNA binding domain and the transactivation domain of a transcription factor or the targeting domain and activity domain of a cell signaling protein), the invention provides a light-regulatable function (e.g., light-regulatable gene transcription, membrane localization, or cell signaling).

In one aspect of the invention, the fusion proteins comprise, consist essentially of, or consist of a protein of interest, a targeting sequence, and a protein light switch fused together, wherein illumination of the fusion protein exposes or hides the targeting sequence. In one embodiment, the fusion proteins comprise more than one targeting sequence. By regulating the exposure of the targeting sequence, delivery of the protein of interest to a target can be regulated. In one embodiment, illumination exposes the targeting sequence. In another embodiment, illumination hides the targeting sequence. By regulating delivery, the skilled artisan can manipulate protein interactions, signaling and other cell functions on a cellular or subcellular basis. One aspect of the invention relates to methods of targeting a protein of interest to a location in a regulatable manner, comprising illuminating the fusion protein to expose or hide a targeting sequence. Id one embodiment, illuminating the fusion protein exposes or hides the target sequence and also activates the protein of interest. In another embodiment, illumination of the fusion protein only exposes or hides the target sequence. In one embodiment, the fusion protein comprises a nuclear localization signal (NLS) or a nuclear export signal (NES) and illumination exposes the signal, thereby causing the fusion protein to move into or out of the nucleus. In another embodiment, the fusion protein comprises both a NLS and a NES, one of which is regulated by the protein light switch. By balancing the strength of the NLS and NES, the location of the fusion protein can be tightly controlled by illumination. In other embodiments, the targeting sequence targets the fusion protein to a subcellular location, such as a membrane (e.g., the cytoplasmic membrane or an organelle membrane, e.g., mitochondrial or endoplasmic reticulum membrane) or a specific structure such as a focal adhesion (e.g., using the FAT domain of FAK kinase to target paxillin).

In one aspect of the invention, the protein of interest is a target protein binding sequence and fusion proteins of the invention comprise, consist essentially of, or consist of a target protein binding sequence fused to a protein light switch, wherein illumination of the fusion protein exposes or hides the target protein binding sequence. The target protein binding sequence can be one that activates or inactivates a target protein. By controlling exposure of the target protein binding sequence with illumination, the skilled artisan can regulate interaction between the target protein binding sequence and the target protein. By regulating the interaction, one can manipulate protein interactions, signaling and other cell functions on a cellular or subcellular basis. One aspect of the invention relates to methods of delivering a target protein binding sequence to a target protein, comprising illuminating a fusion protein to expose the target protein binding sequence, thereby allowing the target protein binding sequence to bind to the target protein. Another aspect of the invention relates to methods of manipulating the activity of a target protein, comprising contacting the target protein with a fusion protein and illuminating the fusion protein to expose the target protein binding site, wherein the fusion protein binds to the target protein and activates or inactivates the target protein. The term "contacting the target protein" encompasses placing the fusion protein and the target protein in the same location in a manner in which they can interact with each other, e.g., in the same solution or in the same cell.

One aspect of the invention relates to a pair of fusion proteins comprising a first fusion protein and a second fusion protein, wherein each fusion protein comprises a protein of interest fused to a protein light switch and the protein light switch comprises a domain that allows the two fusion proteins to dimerize upon illumination. Any dimerization domain that can be regulated by illumination when placed near a LOV domain can be used in the invention. In one embodiment, each protein light switch comprises an aureochrome LOV domain and coiled-coil domain. In the absence of illumination, the LOV domain blocks access to the coiled-coil domain. Upon illumination, the coiled-coil domain is exposed and can dimerize with another coiled-coil domain. In certain embodiments, each fusion protein comprises an identical coiled-coil domain and illumination leads to homodimerization of the two coiled-coil domains. In other embodiments, each coiled-coil domain can have a modified sequence such that the domains do not homodimerize and instead specifically heterodimerize with each other. In one example, amino acid residues at the g and e positions (based on the heptad convention) within the first two heptads of the coiled-coil domain can be mutated to polar residues (in particular glutamic acid or arginine), to create specific hydrogen bonds or a salt bridge between two coiled-coil domains. The ability to heterodimerize in the absence of homodimerization provides a high level of specificity to the protein interaction.

The pair of fusion proteins can be used in methods of regulating the interaction of two proteins of interest. By illuminating the pair of fusion proteins, the attached proteins of interest can be brought into proximity with each other to regulate their interaction. The methods allow the spatiotemporal regulation of the proteins of interest. The methods can be applied to any pair of proteins for which interaction is desired. For example, dimerization of kinases (e.g., receptor tyrosine kinases) can be controlled by tethering an aureochrome light switch to the cytoplasmic tail of the kinase. Enzymes can be activated by bringing together complementary portions of the enzyme protein. Signal transduction pathways can be modified by forcing proteins to come together. Proteins can be transported to subcellular locations using localizing target proteins.

A further aspect of the invention relates to libraries of fusion proteins comprising a library of proteins of interest each fused to a protein light switch (e.g., each fused to the identical protein light switch). The proteins of interest can be any collection of proteins or peptides for which it is desired to identify or screen for particular functions or activities. In certain embodiments, the library of proteins of interest comprises, consists essentially of or consists of random peptides, affibodies, fibronectin monobodies, and/or protein domains. The libraries of fusion proteins can be used to screen for fusion proteins capable of differentially performing a function or activity in the absence and presence of illumination. Examples of functions and activities that can be screened for include, without limitation, protein binding, nucleic acid binding, signaling, translocation, and enzymatic activity. Thus, one aspect of the invention relates to methods for identifying a fusion protein that can manipulate the activity of a target protein in a regulatable manner, comprising contacting the target protein with a library of fusion proteins in the absence and presence of illumination, and identifying fusion proteins that exhibit differential binding to the target protein in the absence and presence of illumination. The term "differential binding," as used herein, refers to increased binding of a fusion protein to a target in the presence of illumination as compared to the level of binding in the absence of illumination or decreased binding of a fusion protein to a target in the presence of illumination as compared to the level of binding in the absence of illumination.

In one embodiment, the library can be screened for peptides that bind to a target when the fusion protein is illuminated, e.g., a peptide that acts as a dimerizer upon illumination. In another embodiment, the library can be screened for peptides that bind to a target when the fusion protein is not illuminated, e.g., a peptide that acts as a releaser upon illumination. For example, the target can be the inhibitory switch region of a kinase (e.g., the p21-binding domain of p21-activated kinase or the Rho-binding domain of Rho kinase). In one embodiment, a directed library of peptides comprising critical residues for LOV interaction and/or helix formation can be screened for activity. For example, peptides that are structured to be embedded in the Jα helix domain of the protein light switch (e.g., containing key residues from the Jα helix that are required for caging by the LOV domain) can be screened for target binding activity. For example, the peptides in the directed library can contain the amino acid sequence TAXXIXXAAXXX (SEQ ID NO:3), wherein X is any amino acid. Any peptide in this library that is identified to have the desired binding activity can be readily inserted into the Jα helix domain of the protein light switch and tested for illumination-dependent activity. In a further embodiment, the peptides to be screened may be present in a linker region of the fusion protein such that the conformation of the peptide is constrained when the fusion protein is in the dark state and not constrained when illuminated. In another embodiment, the invention relates to methods for identifying a fusion protein that can manipulate the activity of a non-protein target in a regulatable manner, comprising contacting the target with a library of fusion proteins in the absence and presence of illumination, and identifying fusion proteins that exhibit differential binding to the target in the absence and presence of illumination. Suitable targets include organic and inorganic molecules. Suitable organic molecules can include but are not limited to small molecules (compounds less than about 1000 Daltons), polypeptides (including enzymes, antibodies, and Fab' fragments), carbohydrates, lipids, coenzymes, and nucleic acid molecules (including DNA, RNA, and chimerics and analogs thereof) and nucleotides and nucleotide analogs.

The library of fusion proteins can be screened using any methods known in the art for screening protein-based libraries, including high throughput screening and surface display of the library (e.g., in an array or by phage display).

The screening assay can be a cell-based or cell-free assay. Further, the library of fusion proteins can be free in solution, affixed to a solid support, expressed on a cell surface, or located within a cell.

With respect to cell-free binding assays, targets can be synthesized or otherwise affixed to a solid substrate, such as plastic pins, glass slides, plastic wells, and the like. For example, the targets can be immobilized utilizing conjugation of biotin and streptavidin by techniques well known in the art. The targets are contacted with the library of fusion proteins and washed. Bound fusion proteins can be detected using standard techniques in the art (e.g., by radioactive or fluorescence labeling of the fusion protein, by ELISA methods, and the like).

Alternatively, the library of fusion proteins can be immobilized to a solid substrate and the targets contacted with the bound library of fusion proteins. Identifying those targets that bind to and/or modulate the library of fusion proteins can be carried out with routine techniques. For example, the library of fusion proteins can be immobilized utilizing conjugation of biotin and streptavidin by techniques well known in the art. As another illustrative example, antibodies reactive with the library of fusion proteins can be bound to the wells of the plate, and the library of fusion proteins trapped in the wells by antibody conjugation. Preparations of targets can be incubated in the fusion protein-presenting wells and the amount of complex trapped in the well can be quantitated.

In another representative embodiment, the library of fusion proteins can comprise a domain that facilitates binding of the fusion protein to a matrix. For example, glutathione-S-transferase fusion proteins can be adsorbed onto glutathione sepharose beads (Sigma Chemical, St. Louis, Mo.) or glutathione derivatized microtitre plates, which are then combined with cell lysates (e.g., $^{35}$S-labeled) and the target, and the mixture incubated under conditions conducive to complex formation (e.g., at physiological conditions for salt and pH). Following incubation, the beads are washed to remove any unbound label, and the matrix immobilized and radiolabel detected directly, or in the supernatant after the complexes are dissociated. Alternatively, the complexes can be dissociated from the matrix, separated by SDS-PAGE, and the level of target found in the bead fraction quantitated from the gel using standard electrophoretic techniques.

With respect to cell-based assays, any suitable cell can be used, including bacteria, yeast, insect cells (e.g., with a baculovirus expression system), avian cells, mammalian cells, or plant cells. In exemplary embodiments, the assay is carried out in a cell line that recombinantly expresses the library of fusion proteins. Further, in other embodiments, it is desirable to use nontransformed cells (e.g., primary cells) as transformation may alter the function of the fusion protein.

In a cell-based assay, the library of fusion proteins to be screened can interact directly with the target (i.e., bind to it) and modulate the activity thereof.

As a further type of cell-based binding assay, the library of fusion proteins can be used as a "bait protein" in a two-hybrid or three-hybrid assay (see, e.g., U.S. Pat. No. 5,283,317; Zervos et al., *Cell* 72:223 (1993); Madura et al., *J. Biol. Chem.* 268:12046 (1993); Bartel et al., *Biotechniques* 14:920 (1993); Iwabuchi et al., *Oncogene* 8:1693 (1993); and PCT publication WO94/10300), to identify other polypeptides that bind to or interact with the library of fusion proteins.

The two-hybrid system is based on the modular nature of most transcription factors, which consist of separable DNA-binding and activation domains. Briefly, the assay utilizes two different DNA constructs. In one construct, a polynucleotide that encodes the target is fused to a nucleic acid encoding the DNA binding domain of a known transcription factor (e.g., GAL-4). In the other construct, DNA sequences encoding the library of fusion proteins ("prey" or "sample") is fused to a nucleic acid that codes for the activation domain of the known transcription factor. If the "bait" and the "prey" proteins are able to interact in vivo, forming a complex, the DNA-binding and activation domains of the transcription factor are brought into close proximity. This proximity allows transcription of a reporter sequence (e.g., LacZ), which is operably linked to a transcriptional regulatory site responsive to the transcription factor. Expression of the reporter can be detected and cell colonies containing the functional transcription factor can be isolated and used to obtain the nucleic acid encoding the fusion protein that binds to the target.

The present invention finds use in veterinary and medical applications. Suitable subjects include both avians and mammals, with mammals being preferred. The term "avian" as used herein includes, but is not limited to, chickens, ducks, geese, quail, turkeys, and pheasants. The term "mammal" as used herein includes, but is not limited to, humans, bovines, ovines, caprines, equines, felines, canines, lagomorphs, etc. Human subjects include neonates, infants, juveniles, and adults. In other embodiments, the subject is an animal model of disease.

The present invention is more particularly described in the following examples that are intended as illustrative only since numerous modifications and variations therein will be apparent to those skilled in the art.

Example 1

Experimental Methods

DNA Cloning: The cDNA encoding the LOV2 domain of *Avena sativa* (oat) phototropin 1 (404-546), including the C-terminal helical extension (Jα), was a gift from Dr. Keith Moffat of the University of Chicago. Chimeric fusion constructs consisting of LOV2-Jα fused to Rac1 or Cdc42 were generated using an overlapping PCR approach so that precise junctional sequences could be engineered without being limited by restriction sites. These included truncations/extensions of the LOV2-Jα C-terminus (539-547), the N-terminus (2-4) of the GTPases, or insertions of designed Schellman caps (KEAGADQI (SEQ ID NO:4) and KELKEAGADQI (SEQ ID NO:5)) (Bystroff et al., *J. Mol. Biol.* 281:565 (1998)). The QuickChange (Stratagene) protocol was used to introduce additional point mutations, including C450A or C450M, and I539E to mimic the dark and lit state of the LOV domain, respectively. PA-Rac1 was constructed as follows: LOV2-Jα (404-546)-Rac1(4-192)/Q61L/E91H/N92H. These constructs were inserted into a pTriEx (Novagen) vector for transient expression in mammalian cells as well as in bacteria. For crystallization, C-terminally truncated PA-Rac1 (A181-192) was subcloned into the pQE-30 vector (Qiagen). Fluorescent proteins mVenus (Nagai et al., *Nature Biotechnol.* 20:87 (2002)), mCherry (Shaner et al., *Nature Biotechnol.* 22:1567 (2004)) and mPA-GFP (Patterson et al., *Science* 297:1873 (2002)) were inserted at the N-terminus of the LOV domain with a short GSGS linker to monitor expression and subcellular localization. After initial characterization, PA-Rac1 with different fluorescent protein tags was subcloned into pBabe-TetCMV vector for retroviral production and establishment of stable MEF Tet-Off cell lines. High fidelity Pfu Turbo DNA polymerase (Stratagene) was used in PCR reactions and all plasmids were verified by DNA sequencing.

Pull-down assay of effector binding: mVenus-tagged LOV2-Jα and Rac1 fusion constructs were coexpressed with FLAG-tagged PAK1 in HEK 293 (LinXE) cells by transient transfection using Fugene 6 (Roche). The cells were lysed in 50 mM Tris pH 7.5, 150 mM NaCl, and 1% Triton X-100 (lysis buffer) with addition of EDTA-free protease inhibitor cocktail (Roche). After brief centrifugation, the supernatants were incubated with FLAG/M2-agarose (Sigma) followed by washes with lysis buffer, and elution with lysis buffer containing 200 μg/ml 3× FLAG peptide (Sigma). All procedures were done at 4° C. under red light, facilitated using Handee spin columns (Pierce). The purified protein complexes as well as cell lysates were fractionated on 4-12% NuPAGE gels (Invitrogen) followed by Western blot analysis using antibodies against fluorescent protein (JL-8, Clontech) and PAK (N-20, Santa Cruz).

Expression, purification and characterization of proteins used for crystallization: C-terminal truncated PA-Rac1 (A181-192) was expressed in *E. coli* strain XL-10 Gold (Stratagene) at 30° C. overnight. All purification steps were done under yellow light at 4° C. Cells were lysed in 20 mM Tris pH 8.5, 50 mM NaCl, 5 mM $MgCl_2$ and 2 mM 2-mercaptoethanol. Protein was purified with a Ni-NTA-FastFlow column (Qiagen) exploiting the N-terminal 6×His tag. The elution was dialyzed against 10 mM Tris pH 8.5, 20 mM NaCl, 5 mM $MgCl_2$ and 2 mM 2-mercaptoethanol. The protein was bound to a MonoQ column (GE Healthcare) and eluted with a linear gradient (0-250 mM NaCl in 50 CV). Fractions containing the protein were concentrated (30 kDa cutoff, Millipore) and further purified by Superose 6 gel filtration chromatography (GE Healthcare, 10 mM Tris pH 8.5, 20 mM NaCl, 5 mM $MgCl_2$, and 2 mM DTE). Prior to crystallization the protein was concentrated to 10 mg/ml (30 kDa cutoff, Millipore). All proteins were characterized spectroscopically. PA-Rac1 showed reversible light dark conversion. The dark recovery rate of PA-Rac1 was measured as described previously (Salomon et al., *Biochemistry* 39:9401 (2000)). The inactive C450A mutation showed no effect upon light illumination whereas truncated C450M (A181-192) was prone to aggregation upon light illumination and, therefore, no data for light dark conversion could be measured.

Crystallization: Crystallization was carried out under dimmed red light at 20° C. PA-Rac1 and its C450A and C450M mutants were crystallized using the vapor diffusion method by mixing equal volumes of protein (10 mg/ml) and precipitant solution (100 mM calcium acetate/100 mM sodium cacodylate/12% (w/v) PEG 8000 or 4% (w/v) PEG 4000/100 mM potassium chloride). Yellow pencil shaped crystals appeared overnight and grew to a final size of 50×50× 1000 μm³ in a week. To avoid photoactivation, crystal handling was done by shielding the microscope light bulb with a 2 mm thick RG630 filter (ITOS, Mainz, Germany). Prior to cooling the crystals in liquid nitrogen they were transferred stepwise to precipitant solution supplemented with 20% (v/v) ethylene glycol for cryoprotection.

Data collection and structure determination: Diffraction data were collected at the X10SA beamline (Swiss Light Source, Villigen, Switzerland) under standard cryogenic settings. Data was reduced using the XDS suite (Kabsch, *J. Applied Crystallography* 26:795 (1993)) (Table 1) and the structure was solved by molecular replacement (McCoy et al., *J. Applied Crystallography* 40:658 (2007)) using subsequently 2VOU (Halavaty et al., *Biochemistry* 46:14001 (2007)) and 1 MH1 (Hirshberg et al., *Nature Structural Biol.* 4:147 (1997)) as the initial models. During several rounds of refinement with PHENIX (Adams et al., *Acta Crystallogr. D Biol. Crystallogr.* 58:1948 (2002)) and manual model building in COOT (Emsley et al., *Acta Crystallogr, D Biol. Crystallogr.* 60:2126 (2004)), FMN, GTP, $Mg^{2+}$, $Ca^{2+}$ and solvent molecules were included in the model. Structures were validated using MOLPROBITY (Davis et al., *Nucleic Acids Res.* 32:W615 (2004)) and PROCHECK (Laskowski et al., *J Applied Crystallography* 26:283 (1993)) (see Table 1 for final statistics).

TABLE 1

| X-ray diffraction data processing and refinement statistics. | | | |
|---|---|---|---|
| | WT | C450A | C450M |
| Data collection | | | |
| Resolution Range (Å) | 50-1.9 (1.95-1.9) | 50-1.6 (1.65-1.60) | 50-2.2 (2.3-2.2) |
| Space group | $P3_221$ | $P3_221$ | $P3_221$ |
| Unit cell parameter (Å) | a = b = 113.88, c = 69.52 | a = b = 112.64, c = 69.31 | a = b = 112.39, c = 69.20 |
| No. of Reflections | 239280 | 1027560 | 95378 |
| Completeness (%) | 99.8 (99.6) | 99.8 (99.5) | 99.5 (99.8) |
| Redundancy | 5.8 (5.8) | 15.4 (12.3) | 3.7 (3.7) |
| Rmerge (%) | 6.7 (54.5) | 6.5 (45.4) | 10.7 (49.9) |
| Mean I/(σ)I | 19.1 (3.7) | 26.2 (5.8) | 11.7 (2.6) |
| Wilson B factor (Å²) | 20.6 | 18.8 | 22.7 |
| Refinement | | | |
| Resolution (Å) | 40-1.9 (1.94-1.9) | 40-1.6 (1.63-1.60) | 40-2.2 (2.28-2.0) |
| Rwork (%) | 16.7 (21.5) | 16.9 (19.1) | 18.6 ( ) |
| Rfree (%) | 19.5 (27.7) | 18.7 (21.0) | 22.6 ( ) |
| R.m.s.d. bond lengths (Å) | 0.009 | 0.009 | 0.006 |
| R.m.s.d. bond angles (°) | 1.2 | 1.3 | 1.032 |
| No. protein atoms | 2608 | 2606 | 2523 |
| No. of ligand atoms | 63 | 75 | 62 |
| No. of $Mg^{2+}$/$Ca^{2+}$/$Cl^-$ atoms | 1/1/0 | 1/0/3 | 1/0/2 |
| No. of Solvent molecules | 313 | 396 | 214 |
| Average B factor, protein atoms, (Å²) | 23.3 | 21.4 | 22.0 |
| Average B factor, ligands (Å²) | 18.0 | 18.2 | 19.6 |
| Average B factor, solvent (Å²) | 33.3 | 36.2 | 27.3 |
| Maximum likelihood based coordinate error (Å) | 0.23 | 0.18 | 0.26 |

TABLE 1-continued

X-ray diffraction data processing and refinement statistics.

|  | WT | C450A | C450M |
|---|---|---|---|
| Ramachandran Plot |  |  |  |
| Favored regions (%) | 98.1 | 98.7 | 98.4 |
| Allowed regions (%) | 1.9 | 1.3 | 1.6 |
| Disallowed regions (%) | 0 | 0 | 0 |

*Numbers in parentheses are for the highest resolution shell

Structural modeling for linker optimization: The Rosetta program (Rohl et al., *Meth. Enzymol.* 383:66 (2004); Das et al., *Annu. Rev. Biochem.* (2008)) was used to predict the dark state structure of LOV2-Rac1 based on the solved crystal structures of dark state LOV2 (Halavaty et al., *Biochemistry* 46:14001 (2007)) (PBD code 2V0U) and Rac1 (Hirshberg et al., *Nature Structural Biol.* 4:147 (1997)) (PBD code 1MH1). Structure prediction simulations were performed on LOV2-Rac1 545-4, 546-4, and 547-4 constructs. In these simulations, the torsion angles of the residues connecting the two proteins were optimized with Monte Carlo sampling. Using the Rosetta domain assembly protocol (Wollacott et al., *Protein Sci.* 16:165 (2007)), we first applied 1000Φ and ψ backbone torsion angle movements of up to 180° each to three residues connecting LOV2 to Rac1 in a low resolution representation. Small backbone torsion angle moves of up to 4° were then performed on a high-resolution representation of LOV2-Rac1, followed by a global repacking of all sidechain rotamers. After every 15 cycles of small moves and repacking, further repacking was restricted to the rotamers at the interface and next to the LOV2-Rac1 linkers. This sequence of refinement was repeated for a total of 150 cycles. Next, we adopted a series of small moves, global rotamer repacking, as well as backbone minimization within 5 residues of the LOV2-Rac1 linker for high-resolution optimization cycles. After every ten cycles, only rotamers at the interface and next to the LOV2-Rac1 linkers were repacked. A total of 100 such high resolution optimizations were used to generate models, which were further scored using Rosetta's energy function. One thousand models, each representing a different folding trajectory, were generated per construct from simulations using the domain assembly protocol.

The complex structure of Rac3 and the CRIB domain of PAK4 (PBD code 2OV2) was used to model the interaction of CRIB-containing effectors with LOV2-Rac1 constructs. The crystal structure of Rac1 (Hirshberg et al., *Nature Structural Biol.* 4:147 (1997)) (1MH1) was superimposed onto the complex structure by mapping the Cα atoms of Rac1 onto those of Rac3. This derived complex structure was then superimposed onto the LOV2-Rac1 models to create model-CRIB complexes. Side chain rotamers at the interface of each complex were optimized using rotamer repacking (Kuhlman et al., *Proc. Natl. Acad. Sci. USA* 97:10383 (2000)). These complexes were scored using the Rosetta energy function. A low-scoring model-CRIB complex indicated the model could bind CRIB, while a high-scoring model-CRIB complex indicated clashes between atoms of the model and the CRIB domain, resulting in reduced binding.

Models generated in a simulation were grouped into clusters according to their pair-wise root mean square deviation (RMSD). The RMSD (in Å) of the Cα atom positions of each model from all other models in the simulation was calculated. Those models falling within a radius of 3 Å RMSD from each other were grouped into a cluster. A cluster member representing the center of each cluster was chosen.

Isothermal titration calorimetry: Dark and lit state mimetics of PA-Rac1, C450A and I539E, were cloned into a pTriEx vector with an N terminal six Histidine tag. Residues 65-150 of PAK1, comprising the extended CRIB domain, were cloned into a pET23 vector, with a C-terminal 6× Histidine tag. All proteins were expressed in *E. coli* strain BL21(DE3) cells (Stratagene) at 16° C. overnight in the dark. Cells were lysed in 50 mM sodium phosphate pH 7.0, 300 mM NaCl, and 5 mM $MgCl_2$. Proteins were purified under yellow light using TALON Metal Affinity Resin (Clontech) and eluted with 150 mM imidazole at pH 7.0. The proteins were dialyzed against 50 mM sodium phosphate, 150 mM NaCl, 7.15 mM 2-mercaptoethanol, 5 mM $MgCl_2$, and 1% glycerol.

ITC experiments were performed by injecting the dark state mutant C450A of PA-Rac1 (0.14 mM) or the lit state mutant I539E (0.13 mM) into the CRIB domain of PAK1 (10 μM) using a Microcal VP-ITC calorimeter at 25° C. Each titration consisted of 29 injections of 10 μL of mutants of PA-Rac1. The baseline of each titration was determined and subtracted from all of the data points. Titration data for the heat change per injection were fitted to a one-site binding model using Origin software (OriginLab).

Cell Culture: HeLa cells (ATCC) and parental MEF/3T3 Tet-Off cells (Clontech) were maintained in DMEM containing 10% FBS following the supplier's culturing instructions. Stable MEF lines were passaged with addition of 1 ng/ml Doxycyclin, sufficient to suppress protein expression under the Tet-CMV promoter. Doxycyclin was removed 24 hours before live cell imaging. It was important to control expression level because small amounts of Rac activity from PA-Rac were apparently present prior to irradiation, as evidenced by increased ruffling at high expression levels. This was likely due to the equilibrium amount of active Rac present in the dark state. For constructs tagged with fluorescent proteins, expression level could be roughly approximated as proportional to brightness/unit area, enabling use of cells with similar expression.

Figure 4:
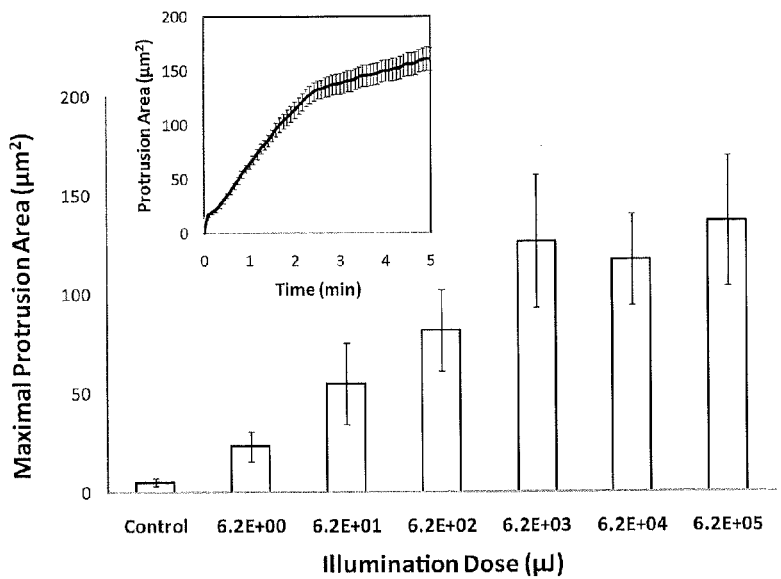
FIG. 4 shows dose-dependent induction of protrusion in MEF cells expressing PA-Rac1. MEF cells expressing mVenus-tagged PA-Rac1 were irradiated in a 10 μm spot with 458 nm laser at the light dose indicated. The lowest dose corresponds to 0.1% of laser power with 10 μs exposure time. Protrusion maps showed extension followed by retraction within 2.5 minutes at all the displayed doses. The maximum area reached within 2.5 minutes was plotted as a function of light dose. This plateaued at 6.2×10$^3$ μJ, reaching a maximal size of 125 μm$^2$. The kinetics of protrusion were remarkably constant, as shown in the inset detailing protrusions for the 6.2×10$^3$ μJ setting. Data are presented as means+/−95% confidence intervals (n=25-50 cells for each power setting and n=50 cells for the inset).

Live cell microscopy: Cells for live cell imaging were seeded on coverslips coated with 5 μg/ml fibronectin in Ham's F-12K medium free of Phenol Red and containing 2% fetal bovine serum (FBS). Coverslips were mounted in an Attofluor live cell chamber (Invitrogen) placed in a microscope stage with a heated stage adapter (Warner). Initial characterization and photoactivation of PA-Rac1, diffusion studies by FRAP and PA-GFP, and protrusion/retraction analyses were carried out using an Olympus FluoView 1000 confocal scanning microscope system equipped with a 60×1.42 NA oil objective and lasers at 405, 458, 488, 515, 568 and 633 nm. Fluorescence images were acquired using 0.1% power from a 30 mW multi-line Ar ion laser (Olympus, minimum power possible without introducing a neutral density filter) and scanned at 2 μs/pixel. The illumination used for photoactivation of PA-Rac1 was between 0.1% power for 10 μs and 1% power for 1 ms in a 10-1 μm spot, at 458 nm. A more precise measure of the light dose used for activation was obtained by measuring the power after the objective using a power meter (Thorlabs), as described below (FIG. 4).

Biosensor images were acquired using an Olympus IX81-ZDC microscope equipped with a CoolSNAP HQ2 14-bit camera (Photometrics) and ET-CFP/YFP filters (Chroma) as described previously (Pertz et al., Nature 440:1069 (2006); Hodgson et al., Meth. Cell Biol. 85:63 (2008)). Bandpass and neutral density filters were switched using motorized filter wheels under computer control (Lud1). CFP, FRET and YFP images Were acquired using a 100 W Hg arc lamp with a 3% ND filter for 500, 250 and 250 ms, respectively. FRET/CFP ratio images were calculated after shading correction, background subtraction, binary masking, and image registration using MetaMorph and MatLab software as described previously (Pertz et al., Nature 440:1069 (2006); Hodgson et al., Meth. Cell Biol. 85:63 (2008); Hodgson et al., Curr. Protocols Cell Biol. (in press)).

Our imaging conditions, exposure times and filters resulted in a donor (ECFP) bleedthrough factor (into the FRET channel) of 0.25 and an acceptor (Citrine) bleedthrough factor of 0.07, using the previously described approach (Pertz et al., Nature 440:1069 (2006); Hodgson et al., Methods Cell Biol 85:63 (2008); Hodgson et al., Curr. Protocols Cell Biol. (in press)). The E-FRET calculation was used as a measure of apparent FRET efficiency of the RhoA biosensor, producing a G factor of 1.57. Photobleaching-corrected FRET efficiency ($E_{corr}$) images were processed based on acceptor photobleaching as previously described (Zal et al., Biophys. J. 86:3923 (2004)). Imaging YFP donor fluorescence of the RhoA biosensor was carried out using bandpass filters 510/20 (excitation) and 545/30 (emission).

Simultaneous photoactivation and biosensor imaging was achieved using the FRAP-3D instrument (MAG Systems), an illumination system with galvanometer-driven laser positioning. A laser source at 473 nm was incorporated into the illumination pathway using beam combining mirrors (Chroma, or a 94%/6% Magic Mirror from Olympus).

FRAP (Fluorescence Recovery After Photobleaching): MEF cells expressing mVenus-tagged PA-Rac1 were irradiated (515 nm, 10% power for 100 μs) at a 10-μm spot using the Olympus FluoView1000 confocal scanning microscope and laser detailed above. The intensity of mVenus fluorescence was monitored (515 nm, 0.1% power for 2 μs) before and after photobleaching at 2 second intervals. The intensity of fluorescence within the bleached spot was normalized against the integrated intensity of the entire cell. The data were plotted and fitted to a single-exponential decay to obtain t½ ($\tau_D$). A t½ of 12.1 s and Fi (immobile fraction) of 18.6±0.6% were obtained (n=26). The diffusion coefficient (D=0.55 μm²/s) was estimated using $D=\omega^2/4\tau_D$ (ω=the radius of the circular bleached spot), assuming exclusively free lateral diffusion (Reits et al., Nature Cell Biol. 3:E145 (2001); Axelrod et al., Biophys. J. 16:1055 (1976)).

PA-GFP tracking: MEF cells expressing mPA-GFP-tagged PA-Rac1 were irradiated (405 nm, 6 mW Diode laser, 10% power for 10 μs) in a 10-μm spot to switch on PA-GFP. The fluorescence of PA-GFP was monitored using a 488 nm laser, acquiring an image every 2 seconds. The intensities of fluorescence within the irradiated spot and an adjacent spot of the same size were quantified and normalized against the entire cell. The decay of activated PA-GFP fluorescence was fitted to a single exponential decay, yielding a t½ of 14.6 s.

Inhibitor studies: MEF cells expressing mVenus-tagged PA-Rac1 were incubated with 1 μM myosin II inhibitor Blebbistatin, 1 μM MLCK inhibitor ML-7, or 10 μM ROCK inhibitor Y-27632 (Calbiochem). Cells underwent the cell shape changes previously described (Katsumi et al., J. Cell Biol. 158:153 (2002)) and then reached a stable state within 30 minutes. After this cells were irradiated with the 458 nm laser at a 10-μm spot to induce PA-Rac activation.

Protrusion/retraction analysis: Fluorescence images of MEF cells expressing mVenus-tagged PA-Rac1 and its mutants were masked based on intensity thresholding to produce binary images. Regions of protrusion were isolated by subtracting the binary image at a given time point from that at time 0. Conversely the binary images of retraction were obtained. Areas not part of protrusions or retractions, those that overlapped the time 0 image, were obtained by subtracting the above two images from that at time 0. Each binary image was assigned a different color: red=protrusion, blue=retraction, green=area overlapping with time 0, and white=background. These operations were carried out using MetaMorph software.

Polarity index calculation: To obtain the polarity index (cos θ) of the migrating MEF cells, X and Y coordinates were obtained for the centroid before movement $(x_0,y_0)$, the centroid after movement $(x_1,y_1)$, and for the center of the irradiation spot $(x_2,y_2)$, using MetaMorph software. The cos and sin values of the angles were obtained using simple triangle calculations. First two angles were defined using an arbitrarily selected horizontal line $\theta_1$=angle between the arbitrary line and the line from $(x_0,y_0)$ to $(x_1,y_1)$, and $\theta_2$=angle between the arbitrary line and the line between $(x_0,y_0)$ and $(x_2,y_2)$. The cos used to characterize polarity (see FIG. 6) was obtained using the following formula:

$$\cos\theta = \cos(\theta_1 - \theta_2) = \cos\theta_1 \cos\theta_2 + \sin\theta_1 \sin\theta_2$$

Example 2

Development of Photomodulated Rac1

Rac and Rho are ubiquitous small GTPases that coordinately regulate motility by orchestrating cytoskeletal behaviors with seconds and submicron precision (Kraynov et al., Science 290:333 (2000); Peitz et al., Nature 440:1069 (2006)). Their mutual regulation remains controversial (Burridge et al., Cell 116:167 (2004)), with data indicating that Rac inhibits and/or activates Rho (Ridley et al., Cell 70:401 (1992); Sander et al., J. Cell Biol. 147:1009 (1999).). They play different, sometimes opposing roles, working together with tight spatial and temporal control to produce cell protrusion and maintain cell polarity (Raftopoulou et al., Dev. Biol. 265:23 (2004); Ridley et al., Science 302:1704 (2003)). We developed a caged Rac to probe localized Rac activation and localized Rac-Rho coordination in living cells. We fused the complete LOV2-Jα sequence of phototropin1 (404-547) to the N-terminus of Rac1, anticipating that the LOV domain in its closed conformation would block the binding of effectors to Rac1 (FIG. 1A), and that light-induced unwinding of the Jα helix would release this steric inhibition, leading to Rac1 activation. Sampling of different junctional sequences in pull down assays revealed that connecting Leu546 of LOV2-Jα to Ile4 of Rac1 leads to substantial reduction in Rac1 binding to its effector PAK (FIG. 1B). To ensure the Rac1 signaling activity was controlled solely by light illumination and that uncaged Rac1 induced no dominant negative effects, mutations were introduced in Rac1 to abolish GTP hydrolysis and diminish interactions with nucleotide exchange factors, guanine nucleotide dissociation inhibitors (Q61L) and GTPase activating proteins (E91H and N92H). This resulted in the photoactivatable analogue of Rac1 (PA-Rac1) used in the following studies. Pull down assays showed that PA-Rac1 has greatly reduced affinity for its effector protein PAK in the dark, as has a PA-Rac1 construct containing a light-insensitive LOV2 mutation (C450A) (Salomon et al., *Biochemistry* 39:9401 (2000)). Effector binding was restored in a PA-Rac1 construct containing a LOV2 mutant (I539E) (Harper et al., *Biochemistry* 43:16184 (2004)) that mimics the unfolded 'lit state' (FIG. 1B).

Using a pull down assay with PAK, a Rac effector, as bait we examined how truncations of Rac or the Jα helix (Jα 539-547, Rac 2-4, FIGS. 2A and 2B) impact Rac-PAK interaction. Connecting Jα Leu546 to Rac Ile4 led to a substantial reduction in effector binding, indicating that this construct is capable of inhibiting Rac activity. The angle between the LOV domain and Rac is also important (FIG. 2A). Substitution of Leu546 by proline (L546P) negated the caging effect, and further reduction of PAK binding was achieved by including rigid structural motifs such as Schellman α-Caps to transition the Jα helix into the first β-strand of Rac at fixed angles (FIG. 2B), although efficient uncaging of the Schellman caps could not be achieved. The LOV546-Rac4 construct induced ruffling, a phenotype of Rac overexpression, in living cells. This was likely due to activation of endogenous Rac1 through sequestration of negative regulatory GAP proteins, as coexpression of dominant-negative Rac1 (T17N) reduced the ruffling. This was eliminated by including the E91H and N92H mutations.

Figures 3A, 3B:
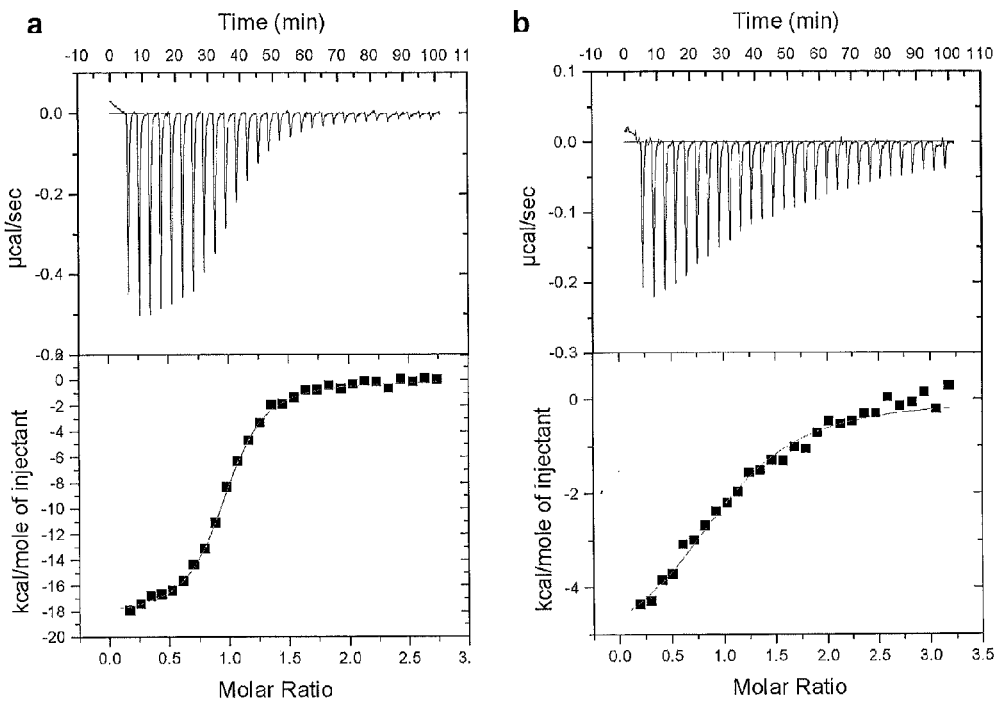
FIGS. 3A-3B show binding of CRIB domain of PAK1 to the dark and lit state mutant of PA-Rac1 in isothermal titration calorimetry. The CRIB domain of PAK1 was titrated with either the lit (FIG. 3A, I539E) or dark (FIG. 3B, C450A) mutant of PA-Rac1. The raw data of heat generated per injection is shown in the top panel, and integrated data of heat output per mole of injected PA-Rac1 mutant versus molar ratio of PA-Rac1 mutant to CRIB is shown at the bottom.
Figures 5A, 5B:
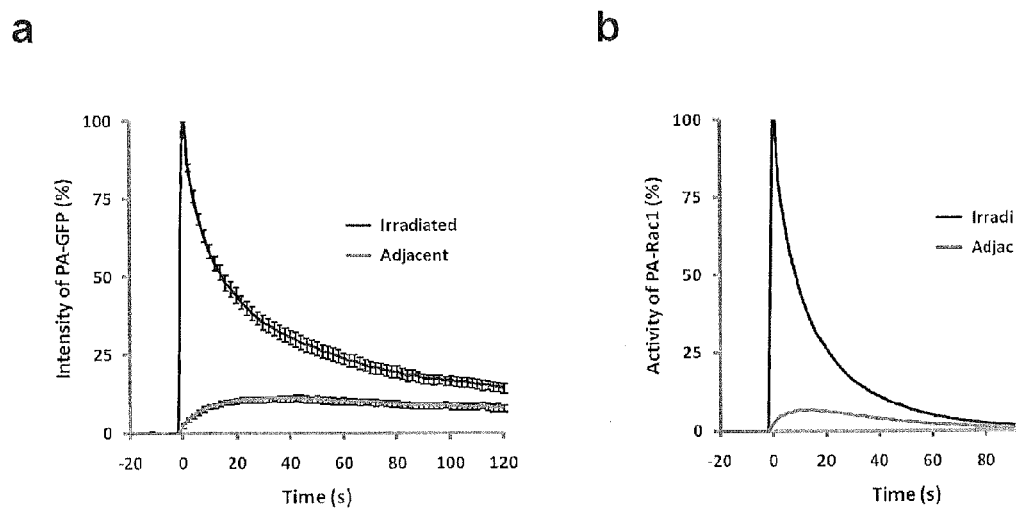
FIGS. 5A-5B show PA-GFP tracking and decay of PA-Rac1 activity. MEF cells expressing PA-GFP tagged PA-Rac1 were irradiated for 10 ns at 405 nm in a 10 nm spot. Fluorescence images (excitation 488 nm) of activated PA-GFP were acquired at 2 s intervals in the irradiated spot and a contiguous spot of equal size.

Isothermal titration experiments were performed to analyze the ability of lit as well as dark state 546-4 to bind the CRIB domain of PAK1. The lit state mimetic, I539E, of 546-4 bound to PAK1 CRIB with an affinity of 220-280 nM. In contrast, the dark state C450A 546-4 mimetic bound PAK1 CRIB with a ten-fold weaker affinity of 2.3-3.1 μM (Table 2 and FIG. 3). Thus, the dark and lit state mutants of PA-Rac1 differed 10-fold in effector binding, with lit state effector affinity similar to that of native Rac (Thompson et al., *Biochemistry* 37:7885 (1998)).

precisely control the subcellular location of Rac activation. We first examined this in mouse embryo fibroblasts (MEF) stably expressing PA-Rac1, and cultured without serum to minimize cell activity prior to irradiation. Irradiation of 20 μm spots at the cell edge generated large protrusions clearly localized next to the point of irradiation (FIG. 1F). Repeated irradiation led first to ruffles and then to protrusion, presumably because accumulation of effector activities downstream of Rac1 was required for protrusion. Movement of the laser spot to different positions led to cessation of ruffling or protrusion at the initial irradiation position and new activities appearing where the laser spot was brought to rest, demonstrating reversible activation. In MEF cells grown with serum, and therefore more prone to movement, complex shape changes were produced by 'painting' the cell with the laser spot. The area of protrusions in MEF cells was dependent on light dosage, indicating the valuable ability to control the level of Rac1 activation (FIG. 4). PA-Rac1 diffusion was analyzed using FRAP (fluorescence recovery after photobleaching) and using PA-Rac1 tagged with photoactivatable GFP (Patterson et al., *Science* 297:1873 (2002)) (FIG. 1E), indicating that PA-Rac1 diffuses more slowly than cytosolic proteins, likely because it is membrane bound (10 μm spot, FRAP D=0.55 μm$^2$/s or $t_{1/2}$=12.1 s; PA-GFP $t_{1/2}$=14.6 s). The half life of dark recovery for PA-Rac1 was determined to be 43 s at room temperature. Simulation using this value indicated that, for two adjacent 10-μm spots, the unirradiated spot will achieve at most 7.5% the activation of the irradiated region (FIG. 1F and FIG. 5). Together these studies validate PA-Rac1 as a robust, genetically encoded and reversible caged protein effective in living cells.

Example 4

Activity of Photomodulated PA-Rac1

We used PA-Rac1 to ask whether localized Rac activation is sufficient to specify cell polarity, generating communica-

TABLE 2

ITC experiments titrating PAK1 CRIB with dark or lit state mutants of PA-Rac1 (Two experiments are shown per mutant).

| Experiment | $K_d$ (μM) | ΔH (Kcal mol$^{-1}$) | ΔS (Kcal mol$^{-1}$ K$^{-1}$) | N |
|---|---|---|---|---|
| C450A | 2.3 ± 0.36 | $-7.0 \times 10^3$ ± 490 | 2.6 | 1.0 ± 0.051 |
| (dark state) | 3.1 ± 0.90 | $-5.6 \times 10^3$ ± 1900 | 6.6 | 0.64 ± 0.18 |
| I539E | $2.2 \times 10^{-1}$ ± $1.4 \times 10^{-2}$ | $-1.8 \times 10^4$ ± 160 | −30.0 | 0.95 ± 0.0057 |
| (lit state) | $2.8 \times 10^{-1}$ ± $5.1 \times 10^{-2}$ | $-1.8 \times 10^4$ ± 360 | −31 | 0.95 ± 0.013 |

Example 3

Photoactivation of PA-Rac1

Figures 6A, 6B, 6C, 6D:
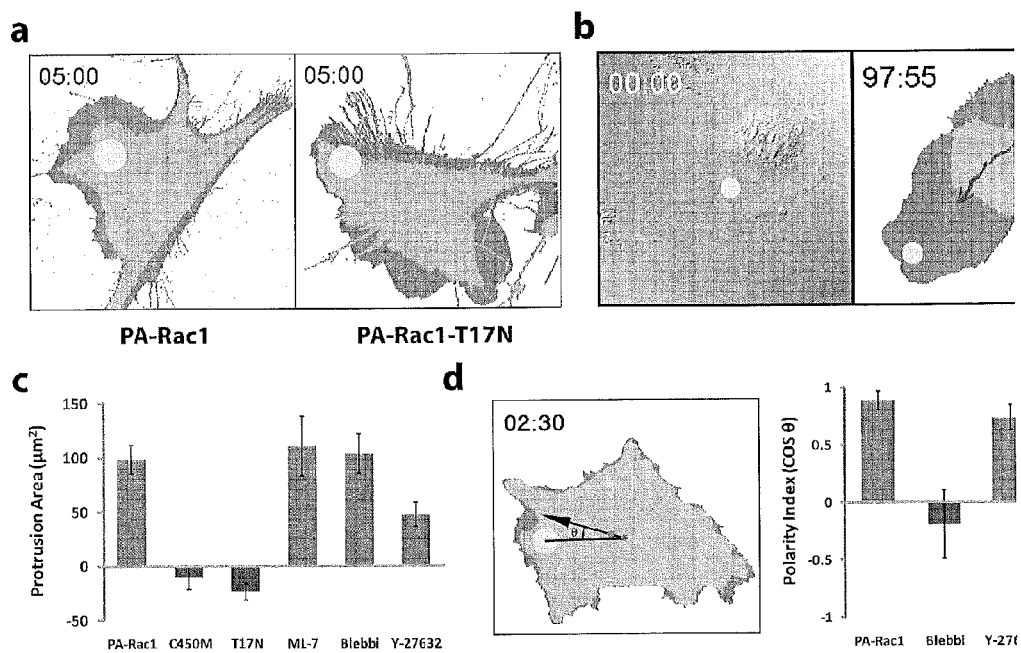
FIGS. 6A-6D show localized activation and inactivation of PA-Rac1 induces migration dependent on ROCK or myosin II.

Activation of PA-Rac1 was examined in HeLa cells expressing a YFP fusion of PA-Rac1 to gauge expression level. The cells remained quiescent when illuminated with wavelengths longer than flavin absorbance (515, 568 or 633 nm), but within seconds after switching to 458 nm, lamellipodial protrusions and membrane ruffles appeared around the cell edges (FIG. 1C). To show that this effect was due to PA-Rac1, kymograms were used to quantify maximum protrusion length. Protrusions from PA-Rac1 cells were four fold longer than those from cells expressing LOV domain alone, or expressing the light-insensitive PA-Rac1-C450A mutant (FIG. 1D). An important advantage of PA-Rac1 is its ability to tion between the front and rear of the cell. In MEF cells, activating Rac1 at one spot near the cell edge not only generated protrusion locally, but also produced retraction on the opposite side of the cell (FIG. 6A). To test whether this cross-cell coordination was due to a gradient of Rac1 activity, rather than mechanical pulling by the protrusions, we fused the LOV domain to a dominant negative mutant of Rac1 using the same linkage as in PA-Rac1. Irradiation of this PA-Rac1-T17N led to nearby retraction rather than protrusion, and now generated protrusion in other areas of the cell (FIG. 6A). The ability of Rac1 alone to control polarized movement was confirmed by repeated irradiation at the cell edge, which could be used to steer prolonged cell movement by generating consistent coordinated extension and retraction (FIG. 6B). In contrast to MEF cells, HeLa cells showed localized protrusion but could not be induced to retract or move simply by activating Rac, indicating that Rac-induced motility is, not surprisingly, subject to modulation by other pathways.

In motility, the GTPase Rho is essential for tail retraction but likely also plays a role at the leading edge, where it appears to be involved in a range of Rac-induced behaviors (Palazzo et al., *Nature Cell Biol.* 3:723 (2001); Tsuji et al., *J. Cell Biol.* 157:819 (2002)). To specifically examine the role of Rho in modulating Rae-induced cell extension, we locally activated Rac while globally inhibiting either ROCK, a downstream effector of Rho, or myosin II, a Rho-regulated protein important in generating actin contractility. PA-Rac1 enabled control of Rac1 activity without the prior cellular compensation seen with other techniques, i.e., mutation or altered expression. Inhibition of ROCK affected Rac-induced protrusion, while inhibition of myosin did not (FIG. 6C). In contrast, the directionality of Rac-induced motility depended on myosin, but not on ROCK (FIG. 6D). These data support a myosin-independent role for Rho and ROCK in Rac1-induced protrusion, potentially through modulating adhesions and traction forces (Beningo et al., *J. Cell Biol.* 153:881 (2001)). Myosin may mediate Rac's control of directionality through induction of tail retraction (Vicente-Manzanares et al., *J. Cell Biol.* 176:573 (2007)), contraction of the cell cortex to direct protrusive force (Burridge et al., *Annu. Rev. Cell Dev. Biol.* 12:463 (1996)), or coupling of actin to adhesions differently at the front and rear (Giannone et al., *Cell* 128:561 (2007)). Rac can control myosin, independent of ROCK, by activating PAK (Sanders et al., *Science* 283:2083 (1999)).

Example 5

Figures 7A, 7B, 7C, 7D:
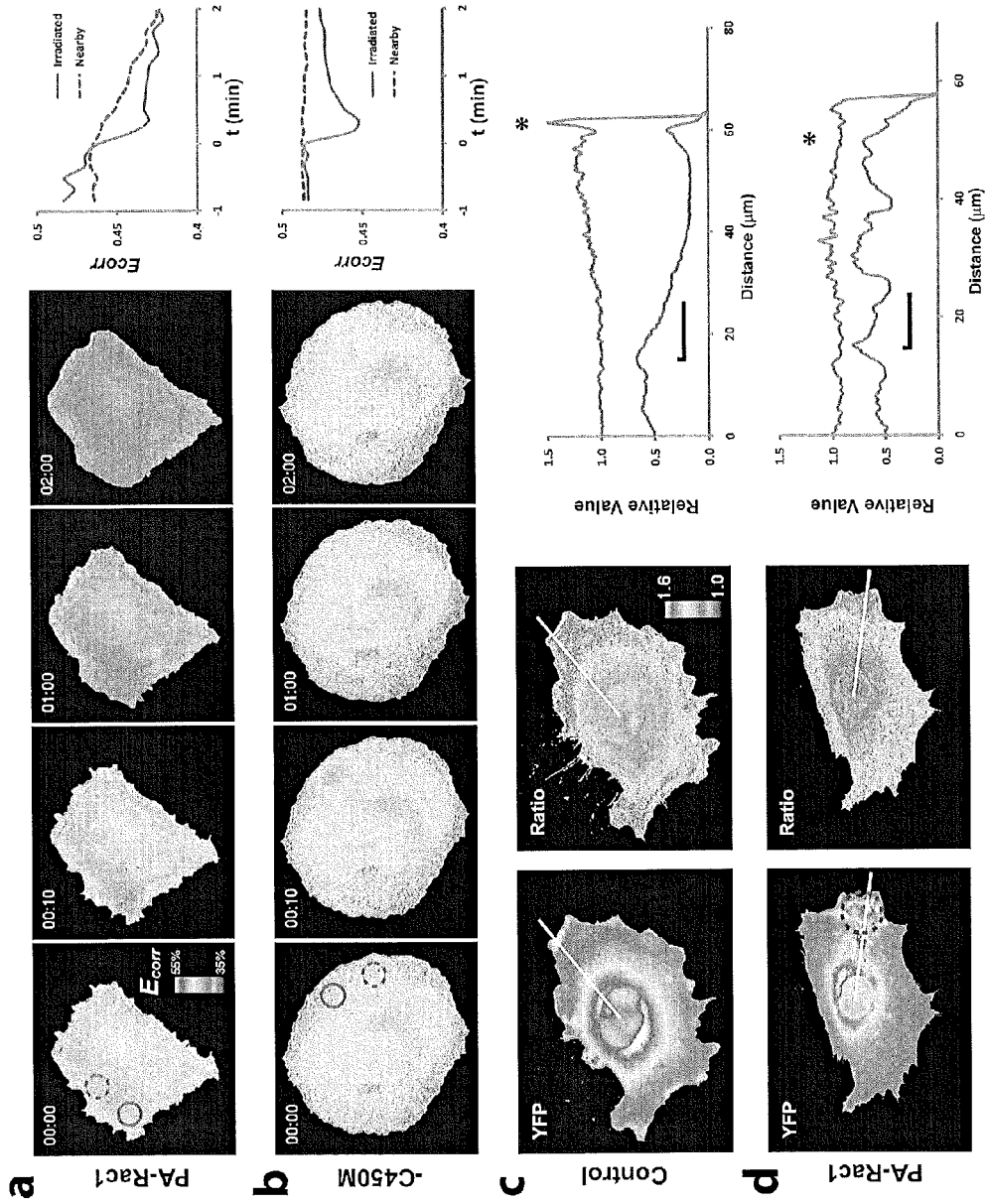
FIGS. 7A-7D show inhibition of RhoA by PA-Rac1.

Regulation of Rho by PA-Rac1

Where and how Rac regulates Rho in vivo remains largely unknown. PA-Rac1 was used together with a fluorescent biosensor of RhoA nucleotide state (Peitz et al., *Nature* 440:1069 (2006)) to directly examine the effects of Rac1 on RhoA in living cells. When PA-Rac1 was activated at a spot within HeLa cells, localized activation of Rac1 led to immediate inhibition of RhoA, and this inhibition spread outward from the irradiated spot (FIG. 7A). This was not simply an artifact of biosensor photobleaching, as irradiating the photo-inactive C450M mutant (FIG. 6C) of PA-Rac1 led to localized biosensor photobleaching and recovery, but no prolonged localized inhibition or 'wave' of inhibition (FIG. 7B). In experiments where repeated pulses of irradiation were used to guide the movement of MEF cells, we noticed striking large ruffles moving from the site of irradiation rearwards towards the nucleus (FIG. 7D). RhoA is normally activated in the constitutive ruffles at the leading edge of moving cells (Pertz et al., *Nature* 440:1069 (2006)) (FIG. 7C), yet the ruffles induced by PA-Rac1 showed RhoA downregulation (FIG. 7D). In control experiments, irradiation of cells expressing the photo-inactive C450M mutant did not produce polarized ruffling or reduce RhoA activity. These studies show that ruffle formation does not require RhoA activity. Furthermore, they suggest compartmentalization of Rac's effects on Rho, as Rac is known to be activated together with Rho at the leading edge (Kraynov et al., *Science* 290:333 (2000); Pertz et al., *Nature* 440:1069 (2006); Kurokawa et al., *Mol. Biol. Cell* 16:4294 (2005)). Mechanisms preventing Rac inhibition of Rho in ruffles are absent when movement is induced solely by Rac. Finally, these observations suggest that Rac can induce translocation of RhoA to the previously described perinuclear reservoir of inactive RhoA (Pertz et al., *Nature* 440:1069 (2006); Kurokawa et al., *Mol. Biol. Cell* 16:4294 (2005)), visible in FIGS. 7C and 7D.

Example 6

Photomodulation of Other GTPases

To understand the structural basis of the PA-Rac1 switch for future application to other proteins, we performed a set of Rosetta structure prediction simulations (Rohl et al., *Meth. Enzymol.* 383:66 (2004)) on a variety of LOV2-Rac1 constructs, and determined high-resolution crystal structures of photo-active and inactive PA-Rac1 in the dark state.

The dark state structures of PA-Rac1 and of the C450A and C450M mutants were determined to a resolution of 1.9, 1.6 and 2.2 Å, respectively (Table 1). The two mutant structures adopt the same fold as the PA-Rac1 protein with an RMSD of 0.21 Å (C450A) and 0.35 Å (C450M) for all Cα atoms. In all structures the effector loop of the Rac1 domain (residues 30-40 of Rac1) is less well defined but the major conformation was built in these models. The solvent accessible side chain of Cys105 located at the end of helix H3 of Rac1 shows additional density in the PA-Rac1 structure arising from a possible modification with DTE but no clear conformation could be included in the structure. Despite a small movement (0.4-0.6 Å) of residues 449-451 to accommodate the larger side chain in the C450M mutant the FMN binding site is identical in all three structures. As in the structure of the isolated LOV domain (PDB code 2V0U), Cys450 adopts a double conformation and shows no bond to the N5 of the FMN. The CE atom of the side chain of the methionine in C450M is in close proximity to the isoalloxazine ring of FMN but does not form a covalent adduct in the dark state.

The connection between the two individual domains, including the Jα helix of LOV2 and the S1 strand of Rac1, is well defined in the electron density. Both domains adopt their previously reported folds (rmsd=0.54 Å, PA-Rac1 Lov2 domain compared to 2V0U; RMSD=0.73 Å, PA-Rac1 Rac1 domain compared to 1 MH1) and inherit their natural ligands FMN and GTP/$Mg^{2+}$ respectively. The interface between the two domains comprises a total buried surface area of 840 $Å^2$ for each domain. Rac1 interfacing residues are located mainly in secondary structural elements including strands 1-4, helix 1 and the $3_{10}$ helix around Pro 69 of Rac1, whereas the interfacing residues of LOV2 are located in the loop regions between strands Aβ and Bβ, Hβ and Iβ, and helices Da and the neighboring loop to helix Ea as well as the C-terminal part of the Jα helix. Compared to 2V0U the N-terminal helix Aα is less pronounced. Residues 403-407 of LOV2 cannot adopt the conformation seen in 2V0U since they would clash with the Rac1 domain of PA-Rac1. These residues are rotated around 180° at Leu408 and are pointing in the direction of the Jα helix.

Figure 8A:
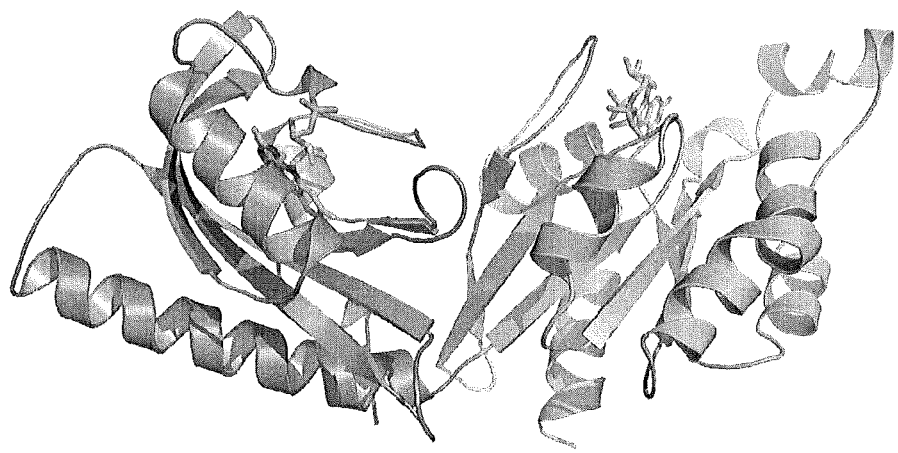
FIGS. 8A-8D show crystallization and structural modeling of PA-Rac1.
Figure 8B:
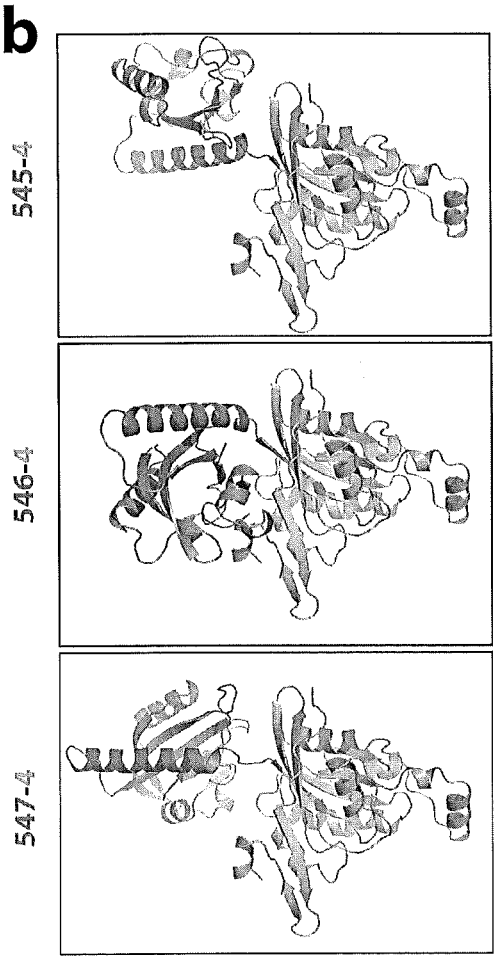
Figure 8C:
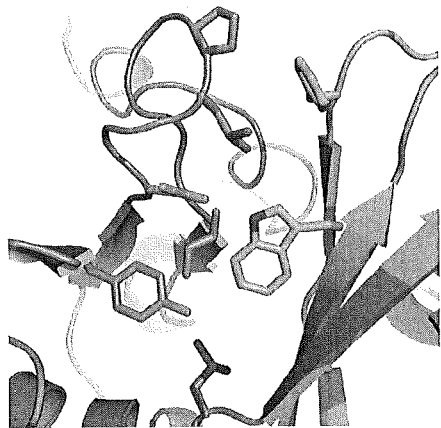
Figure 8D:
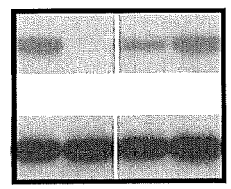

The crystal structure of PA-Rac1 confirmed that the LOV domain occludes effector binding in the dark state (FIG. 8A and Table 1). In the structure, LOV-Jα adopts a closed conformation that superimposes with the recently published structure of isolated LOV-Jα (Halavaty et al., *Biochemistry* 46:14001 (2007)). In the conformational ensemble predicted by simulations of the dark state, the effector binding site of Rac was sterically blocked by the LOV domain in a majority of the low energy models (FIG. 8B, Tables 3-5 and FIGS. 9-12). Consistent with pull down assays (FIG. 1B and FIG. 2A), adding or removing a residue from the connection between LOV and Rac resulted in conformational ensembles with exposed effector binding sites (FIG. 8B). Rac, when held close to the LOV domain in the dark state, forms an extensive interface with the surface of the LOV domain (FIG. 8C). This interaction partially buries the edge strand of the Rac β-sheet, and thereby occludes binding. Given the substantial structural similarity between Rac1 and Cdc42, we hypothesized that the LOV domain could be used to cage Cdc42 in a similar manner as Rac. However, the linkage used for PA-Rac1 (LOV residue 546 linked to Cdc42 residue 4) failed to reduce Cdc42 binding to PAK (FIG. 8D and FIG. 2D). Using the PA-Rac1 crystal structure as a template, a model was built of the Cdc42-LOV dark state.

TABLE 3

Simulations of 546-4 LOV2-Rac1 Construct

| Cluster Number | Members | Score[1] | RMSD from X-ray (Å) | Binds CRIB? |
|---|---|---|---|---|
| 1 | 566 | −512 | 4.5 | No |
| 2 | 151 | −512 | 2.1 | No |
| 3 | 62 | −513 | 7.6 | Yes |
| 4 | 60 | −506 | 4.5 | No |
| 5 | 54 | −503 | 9.0 | Yes |

[1]Average of 10% best scoring decoys

TABLE 4

Simulation of LOV2-Rac1 545-4 Construct

| Cluster Number | Members | Score[1] | Binds CRIB? |
|---|---|---|---|
| 1 | 553 | −509 | Yes |
| 2 | 178 | −509 | Yes |
| 3 | 107 | −507 | Yes |
| 4 | 46 | −508 | Yes |
| 5 | 43 | −509 | Yes |

[1]Average of 10% best scoring decoys

TABLE 5

Simulation of LOV2-Rac1 547-4 Construct

| Cluster Number | Members | Score[1] | Binds CRIB? |
|---|---|---|---|
| 1 | 337 | −507 | Yes |
| 2 | 115 | −500 | Yes |
| 3 | 104 | −508 | Yes |
| 4 | 100 | −508 | Yes |
| 5 | 63 | −491 | Yes |

[1]Rosetta average score of best 10%

One striking result from our study is that the caging of Rac1 is very sensitive to the length of the linker that connects Rac1 to LOV2. Adding or removing a single residue from the linker disrupts caging (FIG. 2A). To determine the physical basis for this length dependence we performed structure prediction simulations with the Rosetta molecular modeling program on three of the constructs (545-4, 546-4, 547-4) used in the dark state pull down experiments. The most prevalent conformation of 546-4 was similar to the crystal structure of 546-4 and contains an extensive interface between Rac1 and LOV2 that is predicted to occlude CRIB binding. A similar interface was not observed in the low energy conformations predicted for 545-4 and 547-4, and the binding site for CRIB is predicted to be accessible in the majority of the low energy conformations.

Models of the dark state 546-4 structure showed a marked difference in quaternary structure from models of 545-4 and 547-4, and importantly, were similar to the crystal structure of PA-Rac1 (FIGS. 9-12). Our lowest RMSD model was 1.7 Å away from the solved crystal structure. Furthermore, the largest cluster of 546-4 models was on average 4.5 Å RMSD away from the solved crystal structure. As in the crystal structure, a well-packed binding interface was formed between the two domains. Residues Leu422, Pro423, Ile428, Tyr508, Leu546 from LOV2 as well as Phe37 and Trp56 of the beta sheet from Rac1 created hydrophobic contacts across the LOV2-Rac1 interface. Residues Asp419 and Trp56 also made a hydrogen bond across the interface. The tight packing of the Rac1 β strand against LOV2 occluded the strand addition binding of CRIB to the Rac1 β sheet.

Figure 11:
FIG. 11 shows models of the LOV2-Rac1 545-4 construct. Models of the five most populated clusters obtained for the 545-4 constructs were analyzed for their abilities to bind the CRIB domain. All 1000 models generated from the simulations were able to bind CRIB. The model in the centre of each of these clusters was overlaid with CRIB domain. The RMSD of these centre models to the X-ray structure of PA-Rac1 were shown (Table 4). Red, Rac1; blue, LOV2; and yellow, CRIB.
Figure 12:
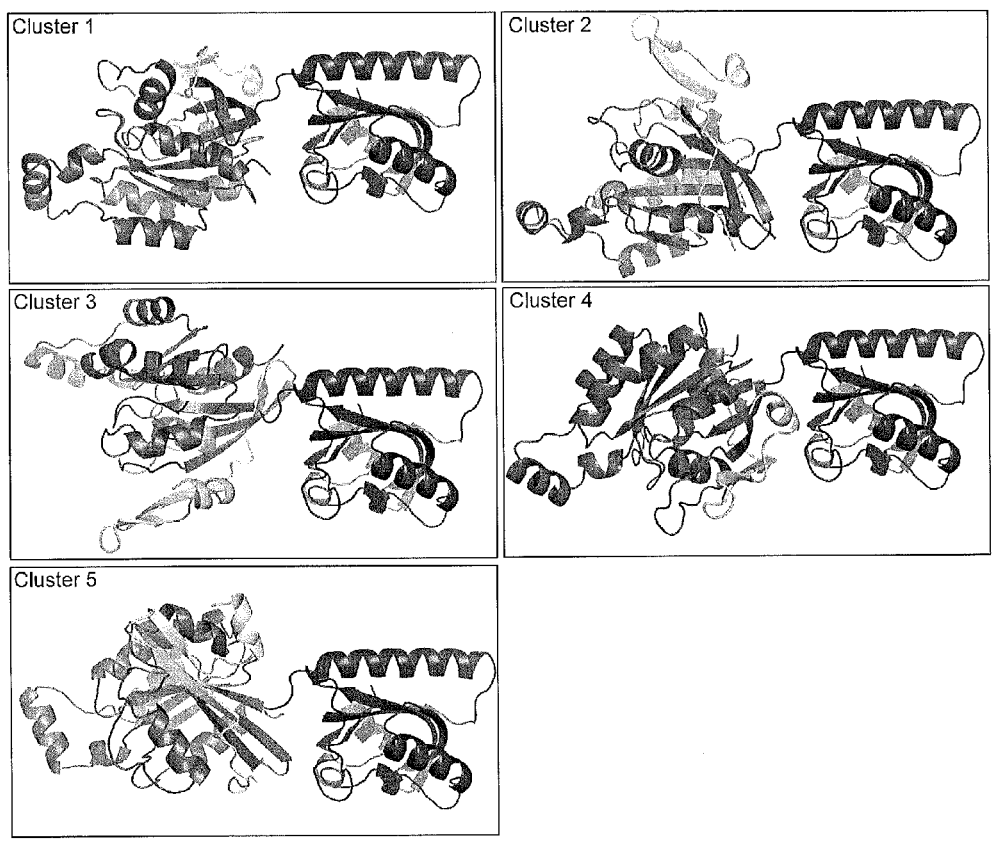
FIG. 12 shows models of the LOV2-Rac1 547-4 construct. Models of the five most populated clusters obtained for the 547-4 constructs were analyzed for their abilities to bind the CRIB domain. Of the 1000 models generated during the simulations, 967 were able to bind PAK4 CRIB. The model in the centre of each of these clusters was overlaid with CRIB domain. The RMSD of these centre models to the X-ray structure of PA-Rac1 were shown (Table 5). Red, Rac1; blue, LOV2; and yellow, CRIB.

An interface did not form in models of the 545-4 construct (FIG. 11). In these models, Rac1 orients away from the LOV2 domain, and thus CRIB is not occluded from binding LOV2-Rac1. Also, a LOV2-Rac1 interface did not form in most of the models of the 547-4 construct (FIG. 12). Clusters generated using the 547-4 simulations contained less models per cluster than all other simulations. Because of the longer linker, 547-4 could sample more conformational space. In the majority of conformations the Rac1 β-sheet was not adjacent to the LOV2 domain and the CRIB domain binding site was predicted to be accessible.

At the interface between Rac and LOV a hydrophobic cluster is formed between residues Phe37 and Trp56 from Rac and Leu422, Pro423, Ile428, Tyr508 and Leu546 from LOV. Consistent with this being a weak, non-evolved interaction, most of the hydrogen bonding potential at the Rac-LOV interface is satisfied by buried and partially buried water molecules instead of inter-domain hydrogen bonds (FIG. 8C). This interface model was used to identify a mutation to Cdc42, Phe56 to Trp at the Rac-LOV interface, that was predicted to stabilize the dark state. Pull down assays show that this mutation substantially improved dark state inhibition of PAK binding, and produced differential affinity for Cdc42 effector in the dark versus the lit state (FIG. 8D). These results indicate that PA-Rac1 can serve as a blueprint for engineering other caged GTPases.

Figure 13:
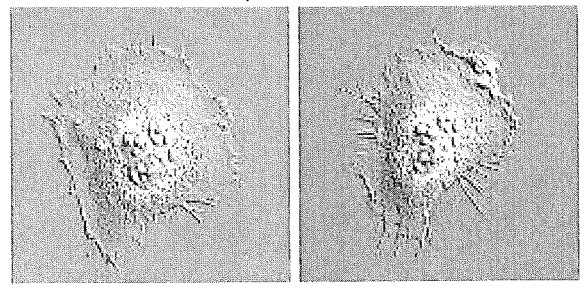
FIG. 13 shows photoactivation of a Cdc42 fusion protein comprising a GTPase binding extension fused to the N-terminus of the LOV2 domain.
Figure 13:
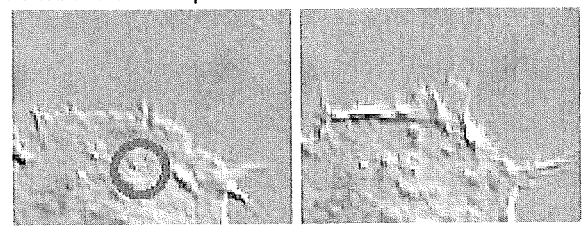
Figure 13:
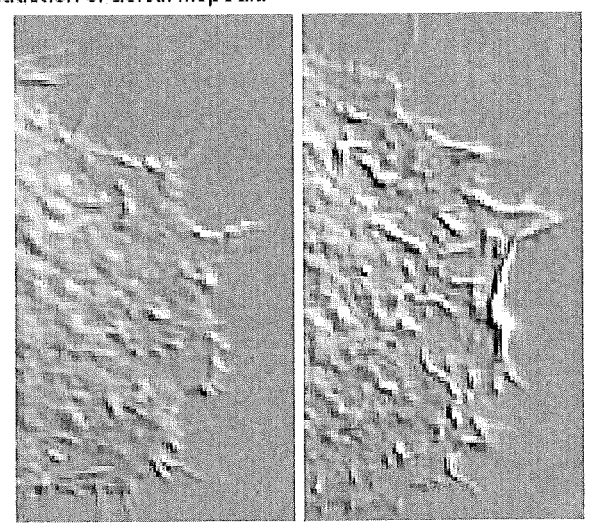
Figure 14:
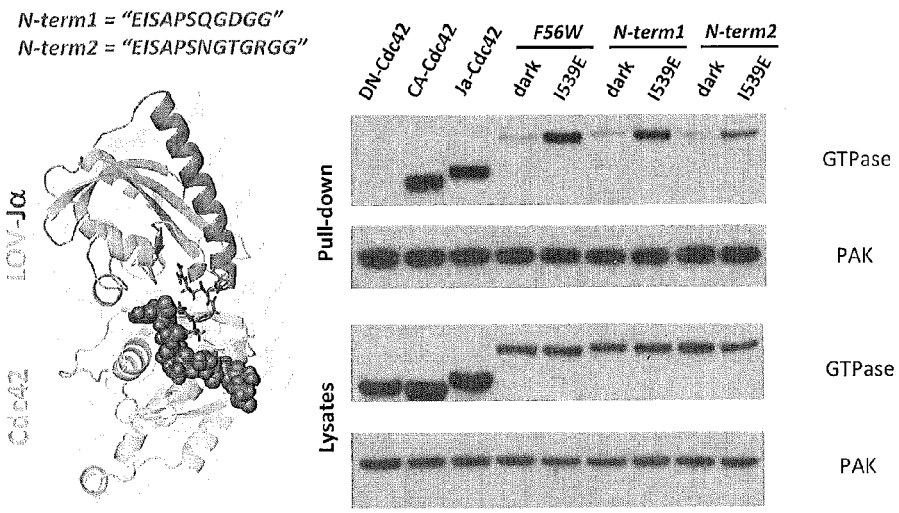
FIG. 14 shows addition of docking sequences derived from the CRIB domain of PAK (N-term1 (SEQ ID NO:14) and N-term2 (SEQ ID NO:2)) negates the need for interface mutations (F56W).

As we learned from the crystal structure of PA-Rac, the transient interaction between the LOV domain and Rac is critical for effective caging of Rac. This led to the successful caging of Cdc42 through the introduction, based on homology, of a point mutation (F56W) that establishes an otherwise non-existing interface between LOV and Cdc42. This strategy, however, is not preferred and is difficult to be extended to other proteins that are distinct from small G proteins. A potentially generalizable approach was developed in which a docking sequence can be designed based on a known target-interacting protein and grafted onto the LOV domain to facilitate the formation of a steric block. The design of the docking sequences and linkers were aided by RosettaDesign. The photoactivatable CDC42 fusion protein was modified by adding at the N-terminus of the LOV domain an extension (amino acid sequence EISAPSNGTGRGG (SEQ ID NO:2)) comprising the GTPase binding sequence EISAP (SEQ ID NO:1). The modified protein was tested in cells as described in Example 2 and exhibited improved qualities, including a decrease in "leaky" activity in the dark state (FIG. 13). The extension, along with a second extension (amino acid sequence EISAPSQGDGG (SEQ ID NO:14)) were tested in a pull down assay and exhibited improved qualities (FIG. 14). These data show that the need for the F56W mutation was negated by addition of the docking sequences.

Example 7

Photomodulation of Vinculin

The ability to regulate the binding of IpaA peptide from *Shigella flexneri* to vinculin was tested by embedding the IpaA peptide sequence in the Jα helix domain of a LOV2 protein light switch. The Rosetta energy function was used to change a portion of the Jα helix domain sequence to the IpaA consensus sequence. The modified helix sequence was DAAEREGVMLIKKTANNIIKAAKDV (SEQ ID NO:6). Using this sequence for the Jα helix domain, two mutant proteins were created. One was a constitutive pseudo-dark state protein comprising a C450A mutation in the LOV2 core that prevents formation of the thiol bond with flavin. The second was a constitutive pseudo-lit state protein comprising I532E and A536E mutations that prevent interaction between the Jα helix and the LOV2 core. When tested by isothermal titration calorimetry, the lit-state mutant was found to have a binding affinity to vinculin of about 30 nM, whereas the dark-state mutant had an affinity of greater than 3 μM, showing that the IpaA fusion protein is an effective light-regulatable vinculin activator.

Example 8

Photoregulatable Nuclear Localization Signal

Figure 15:
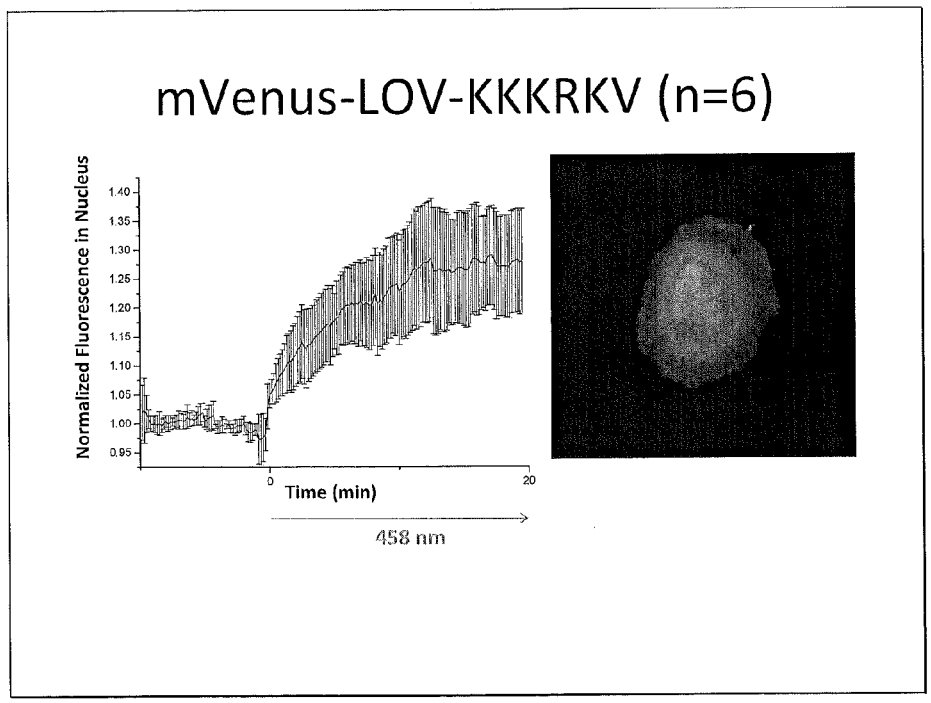
FIG. 15 shows the increase in nuclear fluorescence upon illumination of a cell containing an mVenus-LOV2 fusion protein comprising a nuclear localization signal.
Figure 16:
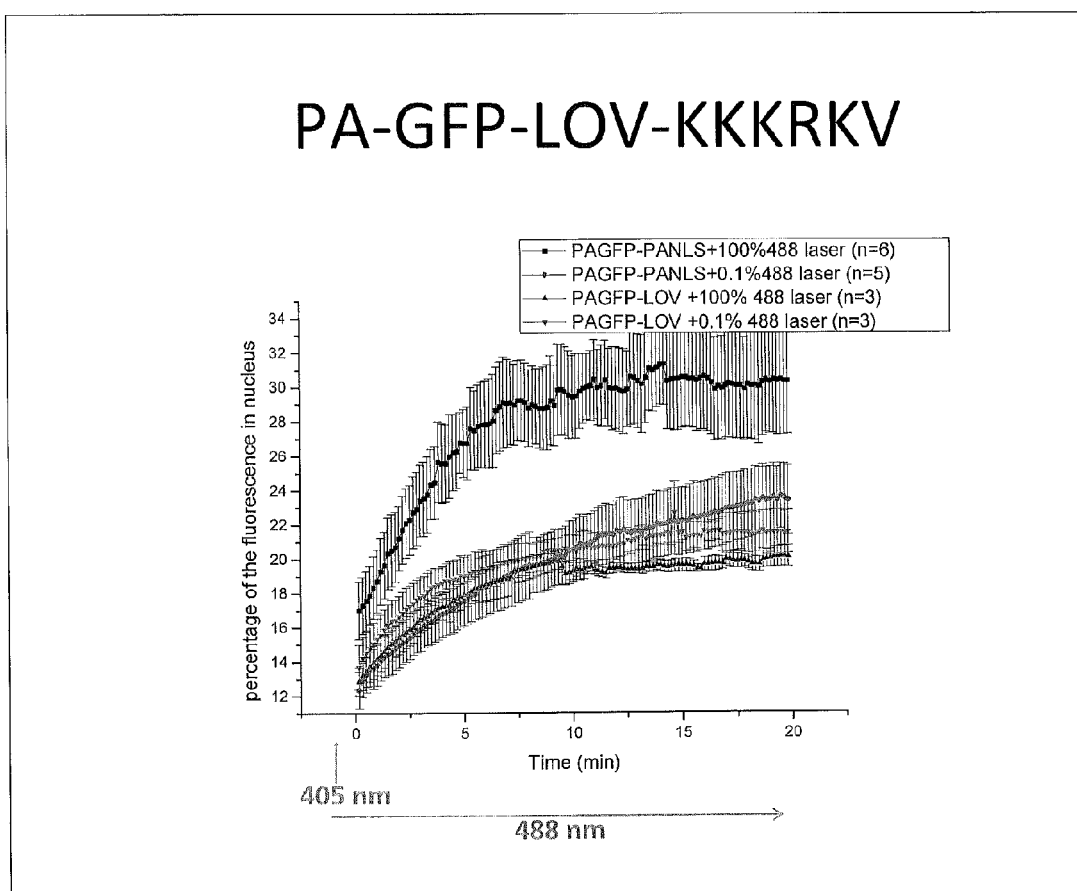
FIG. 16 shows the increase in nuclear fluorescence upon illumination of a cell containing a GFP-LOV2 fusion protein comprising a nuclear localization signal.

In order to create a caged nuclear localization signal (NLS), fusion proteins comprising a NLS consensus amino acid sequence KKKRKV (SEQ ID NO:7) linked to the C-terminus of a wild type LOV2 domain or a mutant constitutive lit state LOV2 domain (I539E) were created. When tested in cells, the wild type fusion protein was predominantly cytoplasmic while the lit state mutant was predominantly located in the nucleus. A fusion protein comprising the fluorescent protein mVenus linked to the N-terminus of the LOV2 domain and the consensus NLS linked to the C-terminus was then tested. Illumination of cells comprising the fusion protein resulted in a 35% increase in fluorescence in the nucleus, indicating that a light-regulated NLS was functional (FIG. 15). Similar results were obtained using a fusion protein comprising PA-GFP-LOV2-NLS, whereas a fusion protein without the NLS (PA-GFP-LOV2) did not exhibit any increase in nuclear localization over background level when illuminated (FIG. 16).

Figure 17:
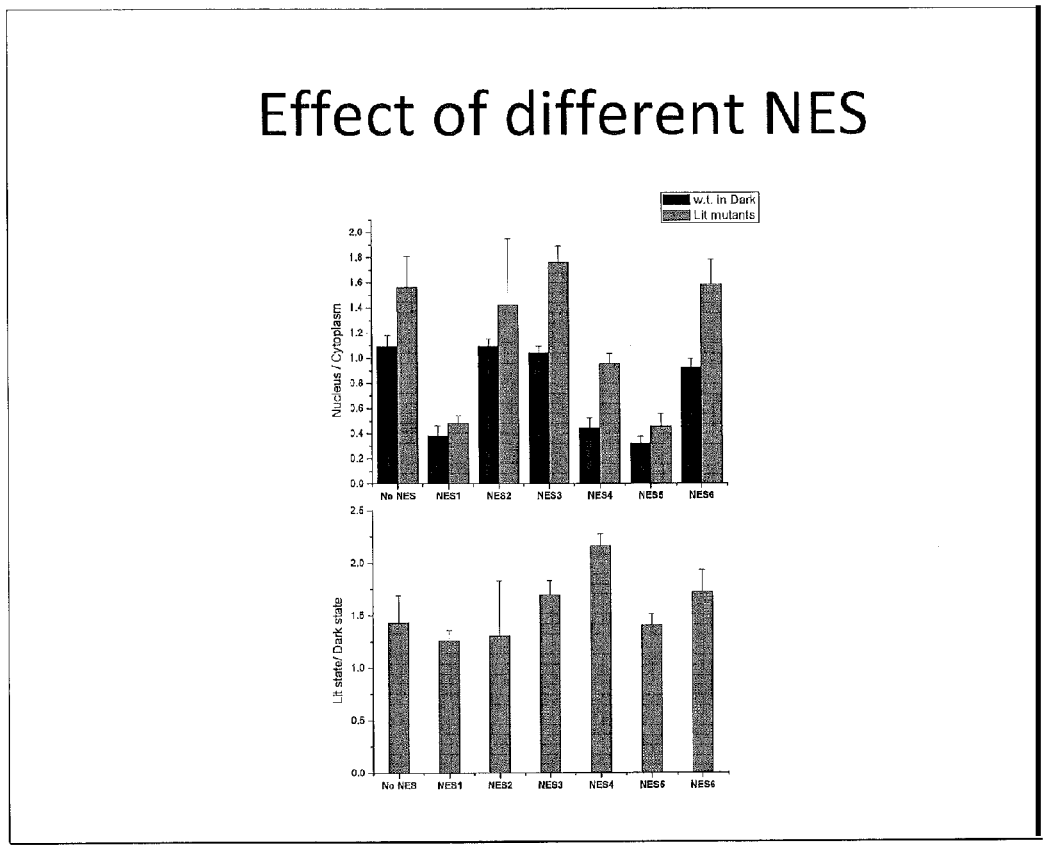
FIG. 17 shows the effect of different nuclear export signals on the illumination-dependent nuclear localization of fusion proteins.

Fusion proteins comprising both a nuclear export signal (NES) and a NLS (NES-Venus-LOV2-NLS) was prepared and expressed in cells to test the ability of the NES to keep the protein in the cytoplasm in the absence of illumination while permitting nuclear localization upon illumination. The NES sequences that were tested are shown in Table 6. Among the different NES sequences, the NES from Smad4a produced the best cytoplasmic:nuclear ratio before and after illumination (FIG. 17).

TABLE 6

|      | Sequence                          | Source                  |
|------|-----------------------------------|-------------------------|
| NES1 | LALKLAGLDI (SEQ ID NO: 8)          | PKI-α                   |
| NES2 | EMFRELNEALELKD (SEQ ID NO: 9)      | p53                     |
| NES3 | SISLSFDESLALCVI (SEQ ID NO: 10)    | Mdm2                    |
| NES4 | GIDLSGLTLQ (SEQ ID NO: 11)         | Smad4a                  |
| NES5 | ESLEEELDVLVLDDEGG (SEQ ID NO: 12)  | P120 catenin isoform 3AB|
| NES6 | SLPHAILRIDLA (SEQ ID NO: 13)       | actin                   |

Example 9

Modified LOV Domain

Figure 18:
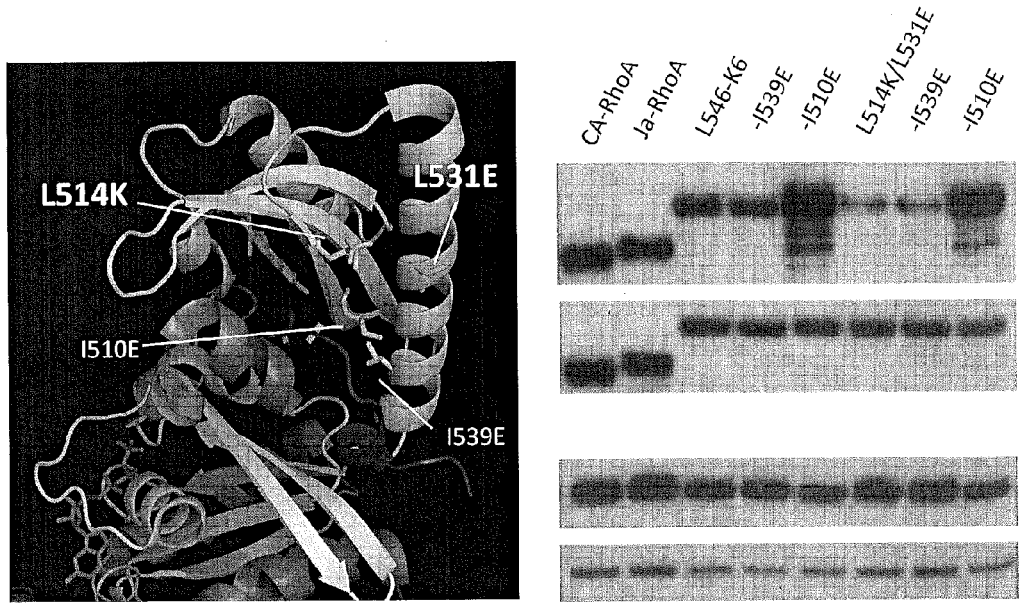
FIG. 18 shows a pair of salt bridge-forming mutations (L514K/L531E) in LOV improves caging.

In our preliminary studies, we found that the LOV domain sometimes non-specifically interacts with some proteins. We suspect that this is due to a few hydrophobic residues on the solvent-exposed surface of the LOV domain, which may be buried in the full length plant phototropin. Two such residues L514 (on LOV) and L531 (on Jα helix) are not known to be involved in either photoconversion or conformational change. Using RosettaDesign, we found these residues can be mutated to polar residues to prevent aggregation. Furthermore, we learned that a hydrogen bond can be established between mutated residues L514K and L531E to stabilize the closed conformation of the LOV-Jα light switch. This led to an improved caging of small GTPases (FIG. 18, compare lane 3 and 6). Because the mutations are within the LOV-Jα sequences, they should benefit caging of other proteins based on LOV-Jα switches.

Example 10

Fusion Proteins with Aureochrome

Figure 19:
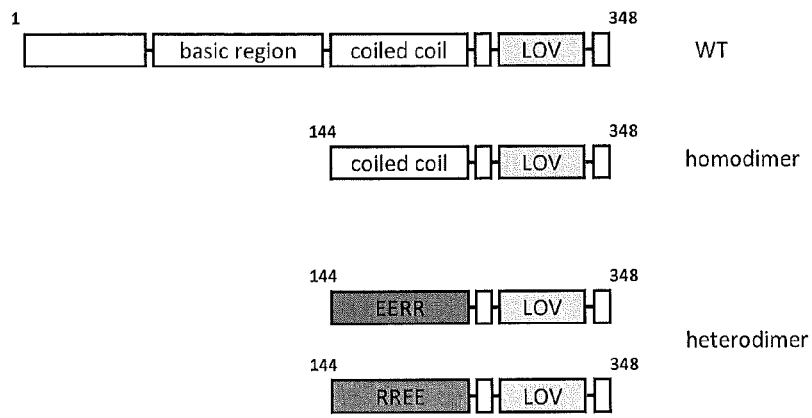
FIG. 19 shows the sequences of aureochrome used for protein engineering.

Aureochrome is a LOV domain-containing photoreceptor identified in stramenopile algae *Vaucheria frigida* that binds to DNA in a light-dependent fashion (Takahashi, F. et al., AUREOCHROME, a photoreceptor required for photomorphogenesis in stramenopiles. *Proc. Natl. Acad. Sci. U.S.A* 104, 19625-19630 (2007)). We characterized the aureochrome protein and found that the sequences containing the coiled-coil domain, the LOV domain, and a short stretch of C-terminal extension are essential and sufficient to mediate light-dependent homodimerization (FIG. 19). By mutating the amino acid residues to polar ones (in particular E or R) at the g and e positions (based on the heptad convention) within the first two heptads of the coiled-coil domain, specific hydrogen bonds can be established between two coiled-coil domains (FIG. 19). This led to the evolution of a pair of aureochrome mutants that fail to homodimerize but favor heterodimerization.

Figure 20:
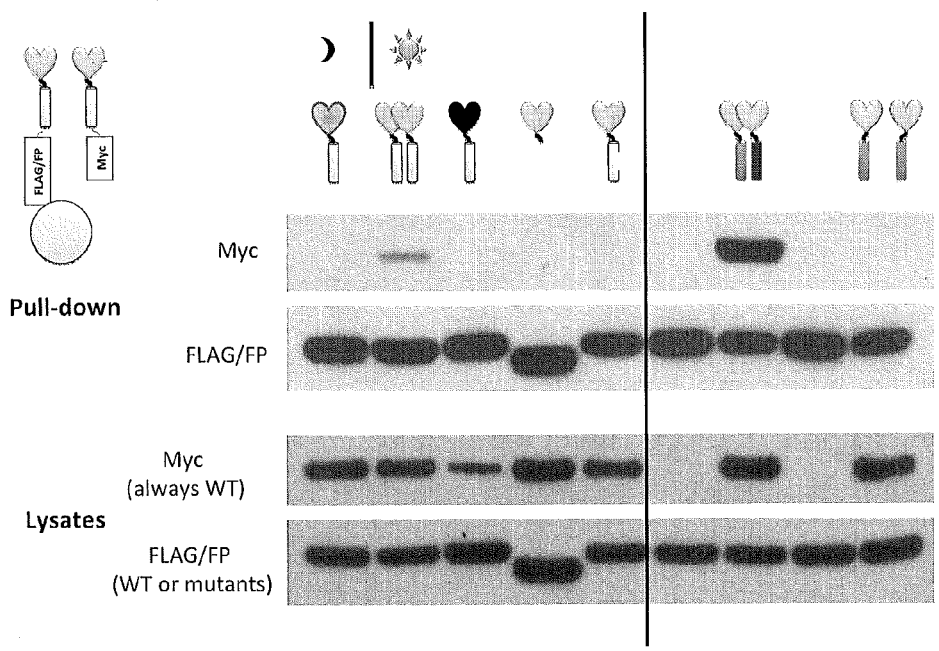
FIG. 20 shows the light-induced dimerization of aureochrome fusion proteins.

A simple pull-down assay was used to demonstrate the light-dependent dimerization of different aureochrome mutants (FIG. 20). As illustrated on the left, different mutants were tagged with either a FLAG tag or a Myc tag, and expressed in HEK293 cells (lysates in bottom two panels). The FLAG-tagged mutants were used as baits and were pulled down with anti-FLAG affinity resin. The precipitates were then blotted for both FLAG ($2^{nd}$ panel) and Myc-tagged proteins (top panel), as an indication of dimerization. When the experiment was performed in the dark, no dimer was detected (lane 1). In contrast, ambient light was sufficient for inducing dimerization (lane 2). The dimerization was dependent on the photoconversion of the LOV domain as a point mutation known to block the photoconversion also prevented dimerization even in the light (lane 3). We also found that the coiled-coil domain is essential for dimerization as deletion or point mutations in the coiled-coil domain disrupted dimerization (lane 4 and 5). The EERR and RREE mutations were sufficient to evolved a pair of aureochrome mutants that failed to homodimerize but favor heterodimerization (lane 7 and 9).

The foregoing is illustrative of the present invention, and is not to be construed as limiting thereof. The invention is defined by the following claims, with equivalents of the claims to be included therein.

The invention claimed is:

1. A fusion protein comprising a protein of interest fused to a protein light switch comprising a light, oxygen or voltage (LOV) domain, wherein illumination of the fusion protein activates or inactivates the protein of interest, and wherein the protein of interest and the protein light switch are not found fused together in nature.

2. The fusion protein of claim 1, wherein the activation or inactivation is reversible.

3. The fusion protein of claim 1, wherein the activation or inactivation is dose dependent.

4. The fusion protein of claim 1, wherein illumination activates the protein of interest.

5. The fusion protein of claim 1, wherein illumination inactivates the protein of interest.

6. The fusion protein of claim 1, wherein the illumination is with visible light.

7. The fusion protein of claim 1, wherein the protein light switch comprises a LOV2 domain.

8. The fusion protein of claim 1, wherein the protein light switch further comprises a Jα domain.

9. The fusion protein of claim 8, wherein the protein of interest is fused in the Jα domain.

10. The fusion protein of claim 1, wherein the protein light switch comprises a fragment of a phototropin.

11. The fusion protein of claim 10, wherein the phototropin is an *Avena sativa* (oat) phototropin 1.

12. The fusion protein of claim 1, wherein the protein light switch comprises a fragment of an aureochrome.

13. The fusion protein of claim 12, wherein the fragment of an aureochrome comprises a LOV domain and a coiled-coil domain.

14. The fusion protein of claim 1, wherein the fusion protein further comprises a linker between the protein of interest and the protein light switch.

15. A method of activating or inactivating a protein of interest present in the fusion protein of claim 1, comprising illuminating the fusion protein.

16. The fusion protein of claim 1, wherein the protein of interest is a mammalian protein.

17. The fusion protein of claim 1, wherein the protein of interest is a human protein.

18. The fusion protein of claim 1, wherein the protein of interest is a first member of a protein binding pair comprising a first member and a second member, wherein binding of the first member to the second member is modulated by illumination.

19. The fusion protein of claim 1, wherein the protein of interest is a functional domain of a protein.

* * * * *

UNITED STATES PATENT AND TRADEMARK OFFICE
CERTIFICATE OF CORRECTION

PATENT NO.         : 8,859,232 B2
APPLICATION NO.    : 13/381383
DATED              : October 14, 2014
INVENTOR(S)        : Hahn et al.

It is certified that error appears in the above-identified patent and that said Letters Patent is hereby corrected as shown below:

In the Specification:

Column 24, Line 43: Please correct "(A181-192)" to read -- (Δ181-192) --

Column 25, Line 6: Please correct "(A181-192)" to read -- (Δ181-192) --

Column 29, Line 2: Please correct "in a 10-1 um spot,"
to read -- in a 10-μm spot, --

Signed and Sealed this
Third Day of March, 2015

Michelle K. Lee
*Deputy Director of the United States Patent and Trademark Office*

SEQUENCE LISTING

```
<160> NUMBER OF SEQ ID NOS: 14

<210> SEQ ID NO 1
<211> LENGTH: 5
<212> TYPE: PRT
<213> ORGANISM: Artificial
<220> FEATURE:
<223> OTHER INFORMATION: GTPase binding sequence

<400> SEQUENCE: 1

Glu Ile Ser Ala Pro
1               5

<210> SEQ ID NO 2
<211> LENGTH: 13
<212> TYPE: PRT
<213> ORGANISM: Artificial
<220> FEATURE:
<223> OTHER INFORMATION: GTPase binding sequence and extension

<400> SEQUENCE: 2

Glu Ile Ser Ala Pro Ser Asn Gly Thr Gly Arg Gly Gly
1               5                   10

<210> SEQ ID NO 3
<211> LENGTH: 12
<212> TYPE: PRT
<213> ORGANISM: Artificial
<220> FEATURE:
<223> OTHER INFORMATION: Directed peptide library sequence
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid

<400> SEQUENCE: 3

Thr Ala Xaa Xaa Ile Xaa Xaa Ala Ala Xaa Xaa Xaa
1               5                   10

<210> SEQ ID NO 4
<211> LENGTH: 8
<212> TYPE: PRT
<213> ORGANISM: Artificial
<220> FEATURE:
<223> OTHER INFORMATION: Shellman cap sequence

<400> SEQUENCE: 4

Lys Glu Ala Gly Ala Asp Gln Ile
1               5

<210> SEQ ID NO 5
<211> LENGTH: 11
<212> TYPE: PRT
<213> ORGANISM: Artificial
<220> FEATURE:
<223> OTHER INFORMATION: Shellman cap sequence

<400> SEQUENCE: 5

Lys Glu Leu Lys Glu Ala Gly Ala Asp Gln Ile
1               5                   10
```

-continued

<210> SEQ ID NO 6
<211> LENGTH: 25
<212> TYPE: PRT
<213> ORGANISM: Artificial
<220> FEATURE:
<223> OTHER INFORMATION: Modified helix sequence with IpaA consensus
      sequence

<400> SEQUENCE: 6

Asp Ala Ala Glu Arg Glu Gly Val Met Leu Ile Lys Lys Thr Ala Asn
1               5                   10                  15

Asn Ile Ile Lys Ala Ala Lys Asp Val
            20                  25

<210> SEQ ID NO 7
<211> LENGTH: 6
<212> TYPE: PRT
<213> ORGANISM: Artificial
<220> FEATURE:
<223> OTHER INFORMATION: NLS Consensus sequence

<400> SEQUENCE: 7

Lys Lys Lys Arg Lys Val
1               5

<210> SEQ ID NO 8
<211> LENGTH: 10
<212> TYPE: PRT
<213> ORGANISM: Artificial
<220> FEATURE:
<223> OTHER INFORMATION: NES1 sequence

<400> SEQUENCE: 8

Leu Ala Leu Lys Leu Ala Gly Leu Asp Ile
1               5                   10

<210> SEQ ID NO 9
<211> LENGTH: 14
<212> TYPE: PRT
<213> ORGANISM: Artificial
<220> FEATURE:
<223> OTHER INFORMATION: NES2 sequence

<400> SEQUENCE: 9

Glu Met Phe Arg Glu Leu Asn Glu Ala Leu Glu Leu Lys Asp
1               5                   10

<210> SEQ ID NO 10
<211> LENGTH: 15
<212> TYPE: PRT
<213> ORGANISM: Artificial
<220> FEATURE:
<223> OTHER INFORMATION: NES3 sequence

<400> SEQUENCE: 10

Ser Ile Ser Leu Ser Phe Asp Glu Ser Leu Ala Leu Cys Val Ile
1               5                   10                  15

<210> SEQ ID NO 11
<211> LENGTH: 10
<212> TYPE: PRT
<213> ORGANISM: Artificial
<220> FEATURE:
<223> OTHER INFORMATION: NES4 sequence

<400> SEQUENCE: 11

```
Gly Ile Asp Leu Ser Gly Leu Thr Leu Gln
1               5                   10

<210> SEQ ID NO 12
<211> LENGTH: 17
<212> TYPE: PRT
<213> ORGANISM: Artificial
<220> FEATURE:
<223> OTHER INFORMATION: NES5 sequence

<400> SEQUENCE: 12

Glu Ser Leu Glu Glu Leu Asp Val Leu Val Leu Asp Asp Glu Gly
1               5                   10                  15

Gly

<210> SEQ ID NO 13
<211> LENGTH: 12
<212> TYPE: PRT
<213> ORGANISM: Artificial
<220> FEATURE:
<223> OTHER INFORMATION: NES6 sequence

<400> SEQUENCE: 13

Ser Leu Pro His Ala Ile Leu Arg Ile Asp Leu Ala
1               5                   10

<210> SEQ ID NO 14
<211> LENGTH: 11
<212> TYPE: PRT
<213> ORGANISM: Artificial
<220> FEATURE:
<223> OTHER INFORMATION: GTPase binding sequence and extension

<400> SEQUENCE: 14

Glu Ile Ser Ala Pro Ser Gln Gly Asp Gly Gly
1               5                   10
```